United States Patent [19]

Robinson et al.

[11] Patent Number: 5,260,292

[45] Date of Patent: Nov. 9, 1993

[54] TOPICAL TREATMENT OF ACNE WITH AMINOPENICILLINS

[75] Inventors: Howard N. Robinson, Lutherville; Neil F. Martin, Potomac, both of Md.

[73] Assignees: Marvin S. Towsend, Rockville; Leonard Bloom, Towson, both of Md. ; part interest to each

[21] Appl. No.: 883,914

[22] Filed: May 12, 1992

Related U.S. Application Data

[63] Continuation-in-part of Ser. No. 664,795, Mar. 5, 1991, abandoned.

[51] Int. Cl.$^5$ .............................................. A61K 31/43
[52] U.S. Cl. ................................... 514/198; 514/192; 514/859; 514/944; 424/401
[58] Field of Search ................ 424/401; 514/859, 198, 514/192, 944

[56] References Cited

U.S. PATENT DOCUMENTS

| | | | |
|---|---|---|---|
| 3,137,620 | 6/1964 | MacDougal | 514/859 |
| 3,896,238 | 7/1975 | Smith | 514/198 |
| 3,952,099 | 4/1976 | Smith | 424/227 |
| 4,003,792 | 1/1977 | Mill et al. | 195/63 |
| 4,039,673 | 8/1977 | Konig | 514/196 |
| 4,097,595 | 6/1978 | Heymes | 424/246 |
| 4,130,667 | 12/1978 | Smith | 424/361 |
| 4,261,962 | 4/1981 | Dauerman et al. | 423/512 |
| 4,289,757 | 9/1981 | Glenn | 514/887 |
| 4,386,080 | 5/1983 | Crossley et al. | 514/859 |
| 4,423,040 | 12/1983 | Rajadhyaksha | 514/859 |
| 4,444,755 | 4/1984 | Horrobin | 514/192 |
| 4,446,145 | 5/1984 | Van Bever | 514/399 |
| 4,492,650 | 1/1985 | Michel et al. | 260/112.5 R |
| 4,496,587 | 1/1985 | Renis | 514/573 |
| 4,537,776 | 8/1985 | Cooper | 514/424 |
| 4,558,008 | 12/1985 | Boech et al. | 435/75 |
| 4,588,692 | 5/1986 | Cunliffe | 435/253 |
| 4,803,069 | 2/1989 | Kekesi et al. | 424/74 |
| 4,898,731 | 2/1990 | Bamberg | 514/198 |
| 4,954,487 | 9/1990 | Cooper | 514/159 |

FOREIGN PATENT DOCUMENTS

| | | |
|---|---|---|
| 1054124 | 1/1967 | United Kingdom . |
| 1587428 | 4/1981 | United Kingdom . |
| 2088717 | 6/1982 | United Kingdom . |
| 2090135 | 7/1982 | United Kingdom . |
| 2207142 | 1/1989 | United Kingdom . |

OTHER PUBLICATIONS

Piamphongsant Int. J. Dermatol. 1985, 24, 441 Abst.
Lubach. Hautarzt. 30, 437 (1979).
Knight. Chem. Abst. 72, 1970, 103688q.
Fisher. Cutis 1980. 25, 474.
Shore, J. Am. Acad. of Dermetol. 4, 604 (1983).
Frank, Postgrad. Med. 61 (6) 92-8 1977.
Chemical Abstracts 15:1572 (1921), "Acne Vaccine Therapy", from J. Am. Med. Assoc., vol. 76, pp. 33-34 (1921).
Pyle, H. D. and Rattner, H., "Contract dermatitis from penicillin," Jour. Amer. Med. Assoc., 1944, V. 125, Jul., p. 901.

(List continued on next page.)

*Primary Examiner*—Thurman H. Page
*Assistant Examiner*—G. S. Kishore
*Attorney, Agent, or Firm*—Leonard Bloom; Marvin S. Towsend

[57] ABSTRACT

A method and composition for topically treating acne and acneiform dermal disorders includes applying an amount of an antibiotic selected from the group consisting of ampicillin, amoxicillin, other aminopenicillins, and cephalosporin, and derivatives and analogs thereof, effective to treat the acne and acneiform dermal disorders. The antibiotic is blended with a carrier suitable for topical application to dermal tissues. The carrier is selected from the group consisting of an aqueous liquid, an alcohol base, a water soluble gel, a lotion, an ointment base, petrolatum, a nonaqueous liquid base, a mineral oil base, a blend of mineral oil and petrolatum, a suspension of solid particles in a liquid, and a suspension of an ion-exchange resin in water.

36 Claims, No Drawings

OTHER PUBLICATIONS

Cohen et al., "Penicillin in Dematologic Therapy", Arch Dermat and Syph, 51:172, Mar. 1945.

Morginson, "The Clinical Use of Penicillin in Dermatology", South. M. J., 38:320326, May 1945.

Franks et al., "Penicillin in the Treatment of Cutaneous Disease", Arch Dermat and Syph, 52:14-16, Jul. 1945.

Hazen, "Acne Indurata in Identical Twins Treated by Penicillin", Arch Dermat and Syph, 53:232-233, Mar. 1946.

Andrews, G. C., Domonkos, A. N., Post, "Treatment of Acne Vulgaris", C. H., J. A. M. A., vol. 146, pp. 1107-1113, (1951).

Stritzler et al., "Acne Necrotica", A.M.A. Arch. Dermat. and Syph, 64:464-469, Oct. 1951.

Robinson, "Role of Antibiotics in Therapy of Acne", A.M.A. Arch. Dermat. and Syph., 69:414-417, Apr. 1954.

Moore, "Systemic and topical treatment of acne vulgaris", Connecticut M. J., 19:93-97, Feb. 1955.

Becker et al., "Evaluation of Antibiotics in the Control of Pustular Acne Vulgaris", A.M.A. Arch. Dermat., 72:157-163, Aug. 1955.

Loveman et al., "The Effect of Antibiotic Therapy Upon Enteric Bacteria in Acne Vulgaris", J Invest Derm, 28(2), Feb. 1957, pp. 183-186.

Frank et al., "Newer Antibiotics in the Treatment of Acne", Antibiotic M., 4(7) Jul. 1957, pp. 419-421.

Stritzler et al., "Significance of the Response of Acne Vulgaris to Antibiotics", Antibiotic M. &CT, 5(2), Feb. 1958, pp. 109-113.

James, "Antibiotic Combination Therapy of Severe Acne Vulgaris", Ohio M J, 54(7) Jul. 1958, pp. 903-905.

Frank et al., "Long Term Therapy of Acne with Antibiotics", New York, J. Med., 59:3237-9, Sep. 1, 1959.

Sulzberger, M. B., Witten, V. H., and Steagall, R., "Treatment of Acne Vulgaris", J. A. M. A., vol. 173, pp. 1911-1915, (1960).

Wansker, "Antibiotics and Pustulocystic Acne", Arch. Derm. (Chicago), 84:96-8, Jul. 1961.

Smith, M. A., Waterworth, P. M., Curwen, M. P., "A Controlled Trial of Oral Antibiotics in the Treatment of Acne Vulgaris", Brit. J. Derm., vol. 74, pp. 86-90, (1962).

Blau et al., "Sodium Oxacillin Treatment of Pyodermas and Acne", Clin. Med., 69:1803-5, Aug. 1962.

Schmitt, C. L., "Current Acne Therapy", Arch. Derm. (Chicago), vol. 87, p. 361, (1963).

Schmitt, "Topical Agents Used in Treatment of Acne", Clin. Med., 70:1473-6, Aug. 1963.

Hewitt, "La Place Des Antibiotiques Dans Le Traitment De L'Acne", Concours. Med., 86:3063-6, May 9, 1964.

Chevert M, "Essaie du staphybiotic dans le traitement de l'acne", [Trial of staphybiotic in the treatment of acne], Sem Ther, Oct. 1964, 40(8) pp. 504-505, in the French language.

Blomquist, "Lokalbehandling av Akne vulgaris", Svensk Lakartidn, 61:3631-4, Nov. 18, 1964, (Swedish).

Stewart et al., "Therapeutic Agents in Acne Vulgaris: Part II. D-Alpha Amino Benzyl Penicillin, Erythromycin and Sulfadimethoxine", Canad. Med. Ass. J., 92:1339-41, Jun. 26, 1965.

Crounse, "The Resource of Acne to Placebos and Antibiotics", J.A.M.A., vol. 193, No. 11, pp. 906-910, Sep. 13, 1965.

Newcomer et al., "Current Topical Therapy for Acne Vulgaris", Wester. Med., 7:Suppl 2:21-6, Apr. 1966.

[Therapeutic experiences with hetacillin in dermatology] Tanioku K; Arata J; Fujita S; Tokumaru N; Miyoshi K; J Antibiot [B], Apr. 1967, 20 (2) pp. 125-6, in the Japanese language.

Koblenzer, "Acne and Antiobiotics", Clin. Pediat. (Phila), 6:563, Oct. 1967.

Chemical Abstracts: 67(7)31499g, for following article: "Dimethylsulfoxide and aspects of its use in dermatology", Rakhmanov, V. A.; Ivanov, O. L.; Potekaev, N. S.; Azhgikhin, I. S.; Konstantinov, A. V.; Yashkul, M. V., I. M. Sechenov 1st Mosk. Med. Inst., Moscow, USSR, in the journal Vestn. Dermatol. Venerol. 1967, vol. 41, No. 2, pp. 13-18 in the Russian language.

"Dimethylsulfoxide and aspects of its use in dermatology", Rakhmanov, V. A.; Ivanov, O. L., Potekaev, N. S.; Azhgikhin, I.S.; Konstantinov, A. V.; Yashkul, M. V., I. M. Sechnov 1st Mosk. Med. Inst., Moscow, USSR, in the journal Vestn. Dermatol. Venerol. 1967, vol. 41, No. 2, pp. 13-18 in the Russian language.

Fulton, J., et al, "Gram-Negative Folliculitis in Acne Vulgaris", Arch Derm, vol. 98, Oct. 1968, pp. 349-353.

Freinkel, "Antibiotics for Acne Vulgaris", Ann. Intern. Med., vol. 71, No. 4, pp. 857-858, Oct. 1969.

(List continued on next page.)

OTHER PUBLICATIONS

Marks, R. and Ellis, J., "Comparative effectiveness of tetracycline and ampicillin in rosacea", Lancet, 1971, vol. 2, pp. 1049-1052.

Leyden, J., Marples, R., Mills, O, Kligman, A., "Gram-negative folliculitis—a complication of antibiotic therapy in acne vulgaris", British Journal of Dermatology, vol. 88, 1973, pp. 533-538.

Becker, "Management of Acne Vulgaris with Antibiotics", Minn. Med., 58(9):657-9, Sep. 1975.

Resh et al., "Topically Applied Antibiotics in Acne Vulgaris", Arch. Dermatol., 112(2):182-4, Feb. 1976.

Grider et al., "Topical Antiobiotics in Treatment of Acne", J.A.M.A., 237(20):2188, May 16, 1977.

Frank, "Treatment of Acne with Topical Antibiotics", Postgrad. Med., 61(6):92-8, Jun. 1977.

Kirk-Othmer, Encyclopedia of Chemical Technology, Third Edition, vol. 2, (1978), p. 812.

M. Gloor, H. Kraft, and M. Franke, "Effectiveness of topically applied antibiotics on anaerobic bacteria in the pilosebaceous duct," Dermatologica, vol. 157, pp. 96-104, (1978).

[Semisynthetic penicillins and lincomycin in the therapy of acne] Polusinteticheskie penitsilliny i linkomitsin v terapii ugrevoi sypi. Shchedrin VI, Vestn Dermatol Venerol, Jun. 1978, (6) pp. 22-26 in the Russian language.

A. Rook et al editors, *Textbook of Dermatology*, 4th Edition, vol. 2, pp. 1605-1617, (1979).

Stoughton, "Topical Antibiotics for Acne Vulgaris", Arch. Dermatol., 115(4):486-9, Apr. 1979.

[Acne fulminans], Acne fulminans, Lubach D; Wrede B; Hautarzt, Aug. 1979, 30 (8) pp. 437-439, in the German language.

Shchedrin, V. I., [Use of various medicinal forms of oxacillin in therapy acne vulgaris], Vestn. Dermatol. Venerol., 1979, Nov., (11):50-2 (English Abstract).

M. Gloor, "Lokale antimikrobielle Aknebehandlung eine Alternative für die systemische Antibiotikatherapie," Fette, Siefen, Anstrichmittel, 82, Jahrgang, Sonderheft, pp. 525-532, (1980).

Stoughton et al., "Topical Antibiotic Therapy of Acne", Cutis, 1980, Feb., 25(2):216-218, 220.

Fisher, "The Safety of Topical Antibiotics in the Treatment of Acne Vulgaris", Cutis, 1980, May, 25(5):474, 476, 481.

"New Topical Antibiotics for Acne", Med Lett Drugs Ther, 1980, Dec. 12; 22(25):107-8.

Hjorth, "Traditional Topical Treatment of Acne", Aceta Derm Venereol [Suppl](Stockh), 1980, Suppl 89:53-6.

Leyden et al., "Topical Antibiotics and Topical Antimicrobial Agents in Acne Therapy", Acta Derm Venereol [Suppl] (Stockh), 1980, Suppl 89:75-82.

Popovich, "Topical Antibiotic Therapy for Acne", Am Pharm, 1981, May; NS21(5):55-8.

Saihan et al., "The Effect of a Topical Antibiotic Preparation in Acne Vulgaris—A Controlled Clinical and Laboratory Study", Br J Clin Pract, 1981, Mar.; 35(3): 106-9.

Adams et al., "The Use of Oral and Topical Antibiotics in Acne", J. Antimicrob Chemother, 1981, Jun.; 7 Suppl A:75-80.

Rapaport, "Topical Antibiotics", Int J Dermatol, 1981, Nov.; 20(9):616-7.

Eady et al., "Topical Antibiotics in Acne Therapy", J Am Acad Dermatol, 1981, Oct.; 5(4):455-9.

Stoughton, "Topical or Systemic Antibiotics for Acne", Int J Dermatol, 1981, Nov.; 20(9):592-3.

Eady et al., "The Use of Antibiotics in Acne Therapy: Oral or Topical Administration?", J Antimicrob Chemother, 1982 Aug.; 10(2):89-115.

Eady et al., "Should Topical Antibiotics Be Used for the Treatment of Acne Vulgaris?", Br J Dermatol, 1982, Aug.; 10(2) 235-46.

Witkowski J. A. and Parish, L. C., "Bacterial skin infections: management of common streptococcal and stapylococcal lesions", Postgrad Med, Oct. 1982, 72 (4), pp. 166-168, 176-178, and 181-185 in the English language.

Kovalev, [Bacteriological Studies in Acne and Rational Selection of Antibiotics for Its Combined Therapy], Vestn Dermatol Venerol, 1981, Jan.; (1):47-50 (Russian with English Abstract).

Shore, R., "Usefulness of ampillicin in treatment of acne vulgaris", Journal of the American Academy of Dermatology, vol. 4, Oct. 1983, pp. 604-605.

Mills, O. H., Kligman, A. M., "Drugs that are ineffective in the treatment of acne vulgaris," British Journal of Dermatology, vol. 108, pp. 371-374, (1983).

(List continued on next page.)

OTHER PUBLICATIONS

Bergey's Manual of Systematic Bacteriology, vol. 2, edited by Sneath et al., pp. 1351-1352, published 1984.

Rook, A., Wilkinson, D. S., et al, *Textbook of Dermatology*, Oxford, Blackwell Scientific Publications, 1984, pp. 1715-1731.

Lane P. R., "Usefulness of ampicillin in the treatment of acne vulgaris" [letter], J Am Acad Dermatol, Apr. 1984, 10 (4), p. 673.

Van Der Meeren et al, "Lokale antibiotica bij acne?", Ned Tijdschr Geneeskd, 1984 Jul. 7; 128(27):1281-4.

Stern et al, "Topical versus Systemic Agent Treatment for Papulopustular Acne", Arch Dermatol, 1984 Dec.; 120(12):1571-8.

Spector, "The Topical and Systemic Treatment of Acne Vulgaris", Iowa Med, 1986 Jun.; 76(6):280-3.

"Cephalosporin for acne vulgaris" [letter], Sheeler R. D., J Am Acad Dermatol, Jun. 1986, 14 (6), p. 1091.

Auld, "Topical Therapy of Acne", Australas J Dermatol, 1986 Dec.; 27(3):118-24.

Bleicher, P., Charles J., and Sober, A., "Topical Metronidazole Therapy for Rosacea", Arch Dermatol, 1987, vol. 123, pp. 609-614.

Poli, F., Prost, C., Revuz, J., "Folliculites A Bacilles Gram Negatif", (in French), Ann. Dermatol. Venereol., 115:797-800. 1988.

Chemical Abstracts 108:215655b (1988).

Hughes et al., "Strategy of acne therapy with long-term antibiotics", Br J Dermatol, 1989 Nov.; 121(5):623-8.

AHFS Drug Information, 1990, Gerald K. McEvoy, editor, published by American Society of Hospital Pharmacists, entry on "Ampicillin", pp. 262-266.

AHFS Drug Information, 1990, Gerald K. McEvoy, editor, published by American Society of Hospital Pharmacists, entry on "Aminopenicillins", pp. 242-254.

AHFS Drug Information, 1990, Gerald K. McEvoy, editor, published by American Society of Hospital Pharmacists, entry on "Amoxicillin", pp. 255-257.

AHFS Drug Information, 1990, Gerald K. McEvoy, editor, published by American Society of Hospital Pharmacists, entry on "Cephalosporins", pp. 82-87.

"Treatment of Teenage Acne", Drug Therapy, Jan. 1991, pp. 56-60.

"Teenage Acne: Clearing Up Misconceptions", Drug Therapy, Jan. 1991, pp. 61-62.

TOPICAL TREATMENT OF ACNE WITH AMINOPENICILLINS

CROSS REFERENCE TO RELATED APPLICATION

The present application is a file wrapper continuation-in-part application of parent application Ser. No. 07/664,795, filed Mar. 5, 1991, entitled TOPICAL TREATMENT OF ACNE, by the same inventors, now abandoned.

FIELD OF THE INVENTION

The present invention relates to the field of treating the skin condition known as acne. More specifically, the present invention is concerned with the prophylactic or therapeutic topical treatment of acne. Even more specifically, the present invention is concerned with the topical treatment of such skin disorders as acne vulgaris, other acneiform dermal disorders, e.g. preadolescent acne, acne rosacea (now known as rosacea), premenstrual acne, acne venenata, acne cosmetica, pomade acne, acne detergicans, acne cosmetica, acne excoriee, gram negative acne, steroid acne, acne conglobata, or nodulocystic acne. The present invention can also be used for topically treating certain other types of acneiform dermal disorders, e.g. perioral dermatitis, seborrheic dermatitis in the presence of acne, gram negative folliculitis, sebaceous gland dysfunction, hiddradenitis suppurativa, pseudo-folliculitis barbae, or folliculitis.

BACKGROUND OF THE INVENTION

Acne vulgaris is a common disease which afflicts approximately 90% of all teenagers, and, not uncommonly, affects men and women in their twenties or thirties or may persist in adults for many years. Acne vulgaris most commonly occurs on oily areas of the skin with high sebaceous gland concentration. The areas of high sebaceous gland concentration are the face, ears, retroauricular areas (e.g. behind the ears), chest, back, and occasionally the neck and upper arms.

Acneiform eruptions can occur wherever there is a pilosebaceous unit or sebaceous follicle which does include the entire surface of the skin.

The basic lesion in acne is the comedo commonly known as the blackhead. The comedo is created by retention of layers of dead skin known as keratin in the lining of the follicles. In addition to hyperkeratosis (which is thickening or retentative layering of keratin), there is an accumulation of sebum which is the lipid-laden product of the sebaceous gland. The cells of the sebaceous glands in which sebum originates are the sebocytes. The combination of the keratin and the sebum produces a plugging of the mouth or opening of the follicular canal, and papules are formed by inflammation around the comedones (plural of comedo). Depending upon the degree of inflammation, pustules, cysts, nodules, granulomatous reactions, scars, and keloids may develop.

Most typical forms of mild acne vulgaris demonstrate the predominance of comedones with the occasional pustules. Pustules and papules predominate in more severe cases. These can heal with scar formation; that is, fibrosis of the lesions which are deep and penetrating. In moderately active cases, larger cystic lesions can develop.

Acne vulgaris can appear in many clinical varieties. The mildest case manifests comedones on oily skin and is called acne comedo.

Papular acne is another variety of acne which has many inflammatory papules. This form of acne is common in adolescent skin, but it can be seen in all ages. The papular inflammatory form of acne can progress to an indurated, deeper, and destructive form known as acne indurata. These lesions can produce severe scarring and can be quite deep seated and destructive.

Steroid acne vulgaris can occur when oral corticosteroids or topical steroids are used and occurs as inflammatory follicular papules. When oral corticosteroids are ingested, the inflammatory papules are usually sudden in appearance and can cover the chest, back, arm, and face. When topical corticosteroids are used for more than two weeks, a localized inflammatory papular response can develop which can proceed to a granulomatous chronic reaction known as steroid acne rosacea.

Premenstrual acne can occur in a large number of menstruating women as a papular and pustular acne vulgaris, approximately one week prior to menstruation. There is a body of evidence that implicates a surge in progesterone as the mediator of premenstrual acne.

Preadolescent acne is divided into neonatal, infantile, and childhood forms of acne. The neonatal form is limited to the first few weeks of life. It usually develops a couple of days after birth. It more commonly afflicts males and reveals transient facial papules and pustules which can clear spontaneously in a few days or weeks. The stimulation of neonatal sebaceous glands by circulating maternal progesterone appears to be the cause.

If the acne persists beyond the first month of life, the acne is called infantile acne and can extend into childhood, adolescence, and adult life. The childhood acne can result from a persistent infantile acne or can develop de novo after age two. This form of acne is uncommon, but it has more of a male predeliction. It is characterized by comedones commonly in groups, papules, pustules, and, rarely, cysts. This condition can extend from a few weeks to several years and can develop into pubertal acne.

Acne venenata is by definition a comedonal or papular acne which occurs after exposure to chlorinated hydrocarbons (chloracne), cutting oils, petroleum oil, coal tar, and pitches.

Acne cosmetica is a persistent low grade comedonal and/or papular and pustular acne that occurs usually on the chin and cheeks of adult women due to oil-based cosmetics, i.e. foundations, facial creams, and sunscreens.

Pomade acne is a type of acne cosmetica which appears to occur almost exclusively in black persons who apply grease and oil to scalp hair and the face as a grooming aid. The lesions are predominately comedonal acne and can develop into inflammatory acne papules, depending upon the chronicity of the pomade use.

Acne detergicans occurs as a type of comedonal acne in patients who use oil-based cleansing soaps. Acne excoriee, also known as pickers acne, starts out as a mild form of papular or comedonal acne which is manipulated or picked and causes further inflammation, more papules, and sometimes scars, pitting, and atrophy of the skin.

Gram negative acne, sometimes called gram negative folliculitis when it extends to the neck, arms, legs, and trunk, is a form of an inflammatory papular, follicular, and pustular response to gram negative organisms including Enterobacter, Klebsiella, Escherichia, Proteus, Serratia, and Pseudomonas. The most characteristic lesion on the face are superficial pustules, or papulo-pustules (which is a combination of a papule and pustule). The face can show diffuse erythema and inflammation surrounding these pustules and juicy papules or papulo-pustules.

The gram negative acne is usually highly resistant and usually occurs in patients who have had inflammatory papular acne for long periods or who have been treated with long term oral administration of antibiotics such as tetracycline, erythromycin, or minocycline or topical antibiotics such as topical clindamycin or topical erythromycin. Subsequent to the oral administration of tetracycline or erythromycin, oral administration of amoxicillin, ampicillin, and trimethoprim-sulfomethoxazole has been shown to be effective in treating this disease. (Poli, F., Prost, C., Revuz, J., Gram-negative Folliculitis, Ann. Dermatol. Venereol., 115:797-800, 1988).

In another reference, Marks, R. and Ellis, J., "Comparative effectiveness of tetracycline and ampicillin in rosacea", *Lancet*, 1971, vol. 2, pages 1049-1052, there is a disclosure that ampicillin has been used orally for treatment of rosacea. More specifically, orally administered ampicillin was compared with orally administered tetracycline in the treatment of rosacea.

Furthermore, in the personal experience of one of the inventors, in his capacity as a practicing dermatologist, in treating well over 200 patients, oral ampicillin taken in the form of an oral capsule between 500 mg and 1 gm each day for one month greatly improves this condition. Before treatment with ampicillin orally, the patients appear to have inflammatory papules and pustules present, and treatment of this clinical subset of acne vulgaris appears to have good success with the oral ampicillin.

However, unwanted side effects often occur with the oral administration of ampicillin (and amoxicillin). For example, unwanted side effects from oral administration often include diarrhea, cramping, and nausea. It would be desirable, therefore, to provide a treatment with ampicillin (and amoxicillin) which does not result in the unwanted side effects stated above.

Acne rosacea is an inflammatory eruption that is chronic and occurs on the face, especially on the nose as well as the scalp and neck, in some instances. It is manifested by erythema, pustules, papules, telangiectasia (which is dilation of superficial capillaries), and hypertrophy of sebaceous glands. The middle portions of the face are most frequently involved. The eyes and eyelids are not uncommonly involved and can produce inflammation and infection of the conjunctiva, eyelids, and hypertrophy of the meibomian glands. Acne rosacea is often called simply rosacea and is most common in middle aged women and men. Rosacea can go on to form a granulamatous rosacea which is characterized by resistant inflammatory papules which when biopsied reveal noncaseating epithelial cell granulomas.

Pseudofolliculitis barbae is a predominantly male affliction which is characterized by inflammatory papules and pustules on the bearded area of the face most commonly in black persons, but all racial groups can be affected. The mechanism is thought to be an inflammatory response to the end of hair (usually curly beard facial hair) into the skin causing a foreign body inflammatory response.

Folliculitis is an inflammatory reaction around the hair follicule which can be bacterial or nonbacterial in nature. Predominately, folliculitis is caused by gram positive organisms such as Staphylococcus and Streptococcus, and less frequently by gram negative bacteria discussed hereinabove with respect to gram negative folliculitis.

Perioral dermatitis is a common papular inflammatory eruption which is confined around the mouth. It most commonly afflicts women in their early twenties to middle thirties, but it can be seen in adolescents and more mature adults.

Hiddradenitis suppurativa is a suppurative (chronic) and cystic disease of apocrine gland regions of the skin, including the axillae, perineum and groin.

There is a genetic tendency to acne, in particular acne congoblata which is a deep cystic and sinus forming type of acne. This condition is essentially a deep, aggressive form of cystic acne occurring in the apocrine gland regions. Topical administration of clindamycin has been used to treat this form of cystic acne.

The etiology of acne vulgaris and related disorders as discussed above is not completely known in every detail. However, what is known is that acne, in general, is caused by a plurality of factors. In general, there are four main factors that cause acne: genetics; hormonal activity; bacteria; and the inflammatory response.

Genetics is a prominent component as it is well known that several members of the same family can be affected with moderate to severe scarring acne. The inheritance by some is thought to be autosomal dominant, but this has not been definitively proven. Furthermore, on the molecular level, there has not yet been discovered a gene or group of genes that are responsible for the various forms of acne vulgaris.

Another key factor in the development of acne is hormonal. In adolescence, for example, it is thought that androgens can interact with receptors on the sebaceous glands and cause stimulation of the sebaceous gland, to hypertrophy and hence form more sebaceous production of lipids and free fatty acids which distend the follicular canal. More specifically, there is evidence for increased peripheral metabolic conversion of the androgen testosterone to dihydrotestosterone at the level of the skin in acne patients. It is further hypothesized that receptors on the sebaceous gland for the active androgen dihydrotestosterone can exhibit various degrees of sensitivity, and that a heightened sensitivity response may be partially or entirely genetically predetermined.

Another causative factor in acne is the presence of bacteria in the follicular canal. Within the follicular canal are bacteria which are indigenous to the follicular lining. Among the bacteria flora present are anaerobic, gram positive organisms called Proprionibacterium acnes. It is interesting to note that they are present in abundance in pathologically affected sites. They are reduced during oral antimicrobial treatment, and their absence from nonhuman animal skin is striking especially since animals do not exhibit acne vulgaris.

Yet another causative factor in acne is the inflammatory response manifested in the skin. More specifically, it is thought that *Proprionibacterium acnes* lives in symbiosis on the keratin lined follicular canal. *Proprionibacterium acnes* ingests the sebum produced from the sebocytes of the sebaceous glands. This nascent sebum is largely lipid in composition and also contains DNA, RNA, proteins, and other cellular components that result from the breakdown of sebocytes themselves. The Proprionibacterium acnes which are highly lipophilic, feed on the nascent sebum. It has been shown that *Proprionibacterium acnes* are found only in sebaceous rich areas. If the nutrients increase due to an active and large sebaceous system, then colonization and high growth rates of *Proprionibacterium acnes* will form. It has been shown that the resident bacterial flora will produce biologically active molecules such as histamine, extracellular enzymes, and peptides which may be responsible for the chemotaxis of the inflammatory infiltrate in acne vulgaris. Since the follicular lining in the pilosebaceous unit is intact, it has been theorized that if colonization of *Proprionibacterium acnes* occurs in sufficient numbers, they could produce initiating antigenic molecules that promote the initiation of inflammation. *Proprionibacterium acnes* can produce proteinases, lipase, and hyaluronate lyase all of which may serve as the catalysts or initiators of the inflammatory infiltrate which has been shown to be composed of neutrophils and lymphocytes.

A number of treatments are presently known for treating acne, some more successful than others. Some modes of treatment have been mentioned above. There are two modes of treatment, topical and systemic.

Aside from treatments mentioned above, some additional systemic treatments for acne that are presently employed are: oral tetracycline; oral erythromycin; minocycline; doxycycline; oral trimethoprim-sulfamethoxazole and isotretinoin.

Those that have been suggested in the past and that are no longer generally employed include: antibacterial vaccines; estrogen therapy; dietary restrictions; and vitamin therapy (e.g. oral ingestion of vitamin A).

Some of the topical treatments that are presently employed are: topical erythromycin, clindamycin, benzoyl peroxide, 2% sulfur, 3% resorcinol, a tetracycline derivative (meclocycline sulfosalicylate 1%), 2% salicylic acid, and tretinoin.

Topical treatments that have been suggested in the past and that are no longer generally employed include: x-ray treatment; electric sparks; vitamin therapy; treatment with a plant extract as described in U.S. Pat. No. 4,803,069.

More specifically with respect to the topical use of certain specific antibiotics, a topical solution, ointment, and gel containing erythromycin is used. Also used is a topical solution, gel, and lotion containing clindamycin, and a cream containing meclocycline sulfosalicylate 1% (a tetracycline derivative).

Some of the undesirable side effects of orally administered antibiotics are abdominal cramps, black tongue, cough, diarrhea, fatigue, irritation of the mouth, loss of appetite, nausea, vomiting, fever, hearing loss, jaundice, rash, rectal and vaginal itching, and superinfection.

It is noted that erythromycin is produced by the bacterium *Streptomyces erytheus* and that erythromycin has a chemical structure that is substantially unique to erythromycin and its derivatives. The molecular weight of erythromycin A is 733.92. The empirical formula for erythromycin A is $C_{37}H_{67}NO_{13}$ having a 60.55% carbon content, a 9.20% hydrogen content, a 1.91% nitrogen content, and a 28.34% oxygen content.

Clindamycin has a chemical structure indicated by its chemical name which is methyl 7-chloro-6,7,8-trideoxy-6-[[(1-methyl-4-propyl-2-pyrrolidinyl)carbonyl]amino]-1-thio-L-threo-alpha-D-galacto-octopyranoside. The molecular weight of clindamycin is 424.98. The empirical formula for clindamycin is $C_{18}H_{337}ClN_2O_5S$ having a 50.87% carbon content, a 7.83% hydrogen content, a 8.34% chlorine content, a 6.59% nitrogen content, a 18.82% oxygen content, and a 7.54% sulfur content.

Other topical treatments for acne using antibiotics are described in the following Great Britain patents: neomycin, G. B. Pat. No. 1,054,124; erythromycin, G. B. Pat. No. 1,587,428; and erythromycin derivatives in conjunction with benzoyl peroxide, G. B. Pat. Nos. 2,088,717 and 2,090,135.

Still another topical treatment for acne, more specifically acne vulgaris, includes preparation of a hyaluronic acid derivative which is a bridged conjugate of hyaluronic acid (which is a linear polymer of N-acetyl glucosamine and glucuronic acid units) bonded to a bridging agent (which is cyanogen bromide) which, in turn, is bonded to the amino-nitrogen atom of the aminopenicillin, ampicillin. Thus, with this hyaluronic acid derivative, the amino-nitrogen of the aminopenicillin is no longer in the form of a primary amino group. This hyaluronic acid derivative is disclosed in Great Britain Published Application 2,207,142.

The formulation disclosed in Great Britain Published Application 2,207,142 may pose several significant problems. First, by reacting the bridging agent with the primary amino-nitrogen of the aminopenicillin, the effectiveness of the aminopenicillin may be severely reduced or even eliminated. More specifically, presently, all of the aminopenicillins that are approved for prescribing in the practice of medicine in the United States include an amino-nitrogen which is in the form of a primary amino group (the nitrogen atom of the primary amino group being bonded to two hydrogen atoms). Not one of these approved aminopenicillins has its characteristic primary amino group modified so that it is no longer a primary amino group.

Another significant potential problem posed by the hyaluronic acid derivative is disclosed in Great Britain Published Application 2,207,142 is the fact that a very toxic bridging agent, cyanogen bromide, is disclosed. Cyanogen bromide can cause toxic effects similar to those of hydrogen cyanide. Hydrogen cyanide may cause death from only a few minutes exposure to a concentration of approximately 300 ppm. (See *Merck Index*, Tenth Edition, 1983, pages 385 and 696) Lesser concentrations may cause headache, vertigo, nausea, and vomiting. With these potentially serious toxic side effects of cyanogen bromide, it may be undesirable if not risky to even employ the hyaluronic derivative disclosed in Great Britain Published Application 2,207,142. More specifically, on page 5, lines 3-5 of Great Britain Published Application 2,207,142, there is a teaching that a stringy precipitate (of a bridged hyaluronic acid/cyanogen bromide/ampicillin conjugate) is washed several times with absolute ethanol and dried in the air. Then, as disclosed on page 5, lines 16-26, the bridged hyaluronic acid/cyanogen bromide/ampicillin conjugate, having been incorporated in a conventional medium, is applied directly to the skin to treat acne vulgaris. What may be risky about using this bridged hyaluronic acid/cyanogen bromide/ampicillin conjugate is that a quantity of unreacted cyanogen bromide may remain as a residue in the precipitate after several rinses with absolute alcohol. Then, by applying some of this bridged hyaluronic acid/cyanogen bromide/ampicillin conjugate directly to the skin of patients, one may then be applying a residue of cyanogen bromide directly to the skin of patients.

For the reasons stated above with respect to the bridged hyaluronic acid/cyanogen bromide/ampicillin conjugate disclosed in Great Britain Published Application 2,207,142, it is desirable to avoid using an ampicillin in which the characteristic amino-nitrogen is not in the form of a primary amino group, and it is desirable to avoid using a material that may contain a toxic residue such as the bridging agent cyanogen bromide.

Still other topical treatments for acne using antibacterials are described in the following U. S. patents: an azole derivative in conjunction with benzoyl peroxide, U.S. Pat. No. 4,446,145, incorporated herein by reference; and metronidazole in a special gel as described in U.S. Pat. No. 4,837,378, incorporated herein by reference.

SUMMARY OF THE INVENTION

Accordingly, it is an object of the invention to provide a new topical treatment for acne and acneiform dermal disorders.

Another object of the invention is to provide a new topical treatment for acne which effectively adds to the armamentarium of physicians, and in particular dermatologists, to treat heretofore resistant forms of acne for which there was no safe, minimal side effect, and effective treatment available.

Another object of the invention is to provide a new topical treatment for acne which will avoid the undesirable side effects of the currently available oral antibiotics for the systemic treatment of acne and acneiform dermal disorders, such as diarrhea, abdominal cramping, nausea, vomiting, drug eruptions, photosensitvity, blood dyscrasias (e.g. depression of white blood cell count and red blood cell count), drug induced hepatitis (elevation of liver functions), and teratogenicity, to name a few.

Another object of the invention is to provide a topical treatment for acne which uses an aminopenicillin whose characteristic amino group is in the form of a primary amino group.

Still another object of the invention is to provide a topical treatment for acne which uses an antibiotic that does not have the risk of bearing a toxic residue of a toxic bridging agent.

These and other objects are achieved by employing the principles of the invention wherein ampicillin, amoxicillin, another aminopenicillin, or other penicillin-like derivative is mixed with a carrier and applied topically to the skin of a patient suffering from acne and other acneiform dermal disorders.

In accordance with the invention described herein, the term aminopenicillin is understood to be an aminopenicillin whose characteristic amino group is in the form of a primary amino group.

Further in accordance with the invention, a cephalosporin or cephalosporin derivative is mixed with a carrier and applied topically to the skin of a patient suffering from acne and other acneiform dermal disorders. Suitable cephalosporins include cefadroxil, cefazolin, cephalexin, cephalothin, cephapirin, cephradine, cefaclor, cefamandole, cefonicid, cefonaride, cefotetan (a cephamycin), cefoxitin (a cephamycin), cefuroxime, the 1-acetyloxy ethyl ester of cefuroxime (cefuroxime axetil), cefoperazone, cefotaxime, ceftazidime, ceftin, ceftizoxime, ceftriaxone, and moxalactam (a 1-oxa-beta-lactam).

With the invention, a variety of treatment regimens are contemplated.

In a first treatment regimen, topical compositions of the invention are used alone to treat the acne and acneiform dermal disorders. In this respect, the topical compositions of the invention can be used as a first line treatment for acne and acneiform dermal disorders.

In a second treatment regimen of the invention, an orally administered antibiotic and a topical composition of the invention are used in combination. There are a number of specific courses of treatment that can be carried out in this second treatment regimen. The oral antibiotic and the topical composition of the invention can be administered simultaneously from the beginning. Or, the oral administration can be begun first, and the topical administration can then be begun. The oral administration can continue when the topical administration begins, or the oral administration can stop when the topical administration begins. Alternatively, the oral antibiotic and the topical composition of the invention can be administered sequentially. With sequential administration, oral administration can take place first, and then topical administration can be begun.

In this respect, after a conventional regimen of treating a patient for acne or acneiform dermal disorders with an orally administered antibiotic, such as tetracycline, minocycline, doxycycline, erythromycin, wherein the patient develops resistance or no improvement, it is the teaching of this invention that an antibiotic selected from the group consisting of ampicillin, amoxicillin, another aminopenicillin, penicillin-like derivatives, and cephalosporin, and derivatives and analogs thereof, is administered topically to the patient.

In a third treatment regimen of the invention, conventional topical medications and topical compositions of the invention can be administered simultaneously. The conventional topical medications which can be used include: benzoyl peroxide and/or topical tretinoin and/or any other topical agent currently used by physicians in the treatment of acne and acneiform dermal disorders.

In a fourth treatment regimen of the invention, conventional oral medications, conventional topical medications, and topical compositions of the invention can be administered simultaneously.

Although the inventors are not bound by any theoretical explanation as to why the compositions and the methods of the invention are efficacious in treating acne and acneiform dermal disorders, presentation of certain theoretical concepts may be of value.

For one thing, it is felt that the efficacy of the compositions and the methods of the invention is due in part to the antibiotic qualities of the compositions employed and the fact that a portion of the topically applied antibiotic is absorbed by the skin and enters the patient's bloodstream.

Another possible reason for the efficacy of the compositions and the methods of the invention is that the compositions of the invention exert an anti-inflammatory effect on the cells of the sebaceous gland unit, thereby decreasing production of neutrophils and lymphocytes which contribute to inflammation.

Still another possible reason for the efficacy of the topical compositions and methods of the invention is that the topically applied antibiotic is able to kill microorganisms that cannot be killed by an orally administered antibiotic. More specifically, the topically applied antibiotic directly kills microorganisms in the sebaceous follicle that are shielded by a hydrophobic sebaceous film inside the follicle from the effects of an antibiotic in the bloodstream. The bloodstream is essentially an aqueous medium, and the hydrophobic sebaceous film blocks the antibiotic in the bloodstream, from diffusing onto the microorganisms on the other side of the sebaceous film. However, the microorganism may produce products that are fat soluble and are able to cross through the sebaceous film and thereby irritate the cells lining the sebaceous follicle. Thus, the hydrophobic sebaceous film may allow passage, in one direction, of irritants from the microorganisms to the follicle walls, but the hydrophobic sebaceous film prevents passage of antibiotic in the bloodstream from diffusing across the hydrophobic sebaceous film in the other direction to the microorganisms.

DETAILED DESCRIPTION OF PREFERRED EMBODIMENTS

It is understood herein that the term penicillin-like derivative is a compound that contains the following chemical structural components: 6-[R-carbonyl)amino]-3,3-di-methyl-7-oxo-4-thia-1-azabicyclo[3.2.0]heptane-2-carboxylic acid, where R is a reactive group substituted on the carbonyl carbon on the nitrogen atom of the 6-amino group.

Ampicillin is an aminopenicillin. Generally, aminopenicillins are semisynthetic penicillin derivatives produced by acylation of 6-aminopenicillanic acid (6-APA). Aminopenicillins have a free amino group (a primary amino group) at the alpha-position on the penicillin nucleus which results in enhanced activity against gram-negative bacteria compared with natural penicillins and penicillinase-resistant penicillins. It is noted that for ampicillin there is a benzylamine group on the carbonyl carbon on the nitrogen atom of the 6-amino group. More specifically, for ampicillin, the "R" in the formula for penicillin-like derivatives is a benzylamine group. Stated somewhat differently, for ampicillin specifically and for aminopenicillins generally, the R group includes a carbon atom bonded to the carbonyl-amino carbon atom, where a primary amino group is bonded to that carbon atom bonded to the carbonyl-amino carbon atom.

Other names for ampicillin include the terms ampicillin A, BRL 1341, P 50, Ay 6108, Adobacillin, Alpen, Amfipen, Ampi-Bol, Bonapicillin, Grampenil, Guicitrina, Copharcilin, Nuvapen, Synpenin, Viccillin, Ultrabion, Ampipenin, Amplisom, Amimed, Ampy-Penyl, Totalciclina, Amipenix S, Amblosin, Ampicin, Amplital, Austrapen, Binotal, Britacil, Doktacillin, Marsilan, Pen-Bristol, Penbritin, Penbrock, Penicline, Pentrex, Pentrexyl, Ponecil, Polycillin, QI Damp, Toliocillin, Totacillin, and Totapen.

Amoxicillin is another aminopenicillin. It is also noted that for amoxicillin there a 4-hydroxybenzylamine group substituted on the carbonyl carbon on the nitrogen atom of the 6-amino group. More specifically, for amoxicillin the "R" in the formula for penicillin-like derivatives is a 4-hydroxybenzylamine group.

Other names for amoxicillin include the terms amoxycillin, AMPC, Amolin, Amopenixin, Amoxi, Amoxipen, Anemolin, Aspenil, Bristamox, Delacillin, Efpenix, Ibiamox, Piramox, and Sumox.

It is noted that both ampicillin and amoxicillin include "R" groups comprised of benzylamine and 4-hydroxybenzylamine groups, respectively. More generically, in accordance with the invention, compositions containing penicillin-like derivatives where "R" in the formula above is benzylamine and derivatives thereof.

Stated somewhat differently, compositions of the invention and the use thereof include ampicillin and derivatives thereof and amoxicillin and derivatives thereof. Also, the compositions of the invention and the use thereof include ampicillin, amoxicillin, or pharmaceutically acceptable salts or solvates thereof.

Suitable forms of ampicillin and amoxicillin can be selected from the group consisting of ampicillin; ampicillin, monohydrate; ampicillin, potassium salt; ampicillin, sesquihydrate; ampicillin, trihydrate; ampicillin, anhydrous form; ampicillin, sodium salt; ampicillin, D(−)form, L(+)form, or DL-form; other suitable ampicillin derivatives; amoxicillin; amoxicillin trihydrate; amoxicillin hydrochloride trihydrate; amoxicillin beta-naphthalenesulfonate trihydrate; and other suitable amoxicillin derivatives.

Other suitable aminopenicillins include bacampicillin and cyclacillin.

Suitable forms of other penicillin-like derivatives or analogs can be selected from the group consisting of azlocillin; acylureido penicillins related to azlocillin; carbenicillin; carbenicillin, disodium salt; carbenicillin, indenyl; cloxacillin; dicloxacillin; dicloxacillin, sodium salt; floxacillin; isoxazolyl penicillins; hetacillin; methicillin; methicillin, sodium; mezlocillin; mezlocillin, sodium salt; nafcillin oxacillin; oxacillin, sodium salt; penicillin BT; penicillin BT, procaine salt; penicillin G; penicillin G benethamine; penicillin G benzathine; penicillin G benzhydrylamine; penicillin G calcium; penicillin G hydrabamine; penicillin G potassium; penicillin G procaine; penicillin N; penicillin N, barium salt; penicillin O; penicillin O, 2-chloroprocaine salt monohydrate; penicillin O, potassium salt; penicillin O, procaine salt; penicillin O, sodium salt; penicillin S potassium; penicillin V; penicillin V, potassium salt; penicillin V, sodium salt; penicillin V, calcium salt; penicillin V benzathine; penicillin V hydrabamine; and phenethicillin.

More specific descriptions of some of the preferred penicillin-like derivatives or analogs are as follows.

Ampicillin has a chemical structure indicated by its chemical name which is 6-[(aminophenylacetyl)amino]-3,3-dimethyl-7-oxo-4-thia-1-azabicyclo[3.2.0]heptane-2-carboxylic acid. The molecular weight of ampicillin is 349.42. The empirical formula for ampicillin is $C_{16}H_{19}N_3O_4S$ having a 55.0% carbon content, a 5.48% hydrogen content, a 12.02% nitrogen content, a 18 32% oxygen content, and a 9.18% sulfur content.

Amoxicillin has a chemical structure indicated by its chemical name which is 6-[[amino(4-hydroxyphenyl)acetyl]amino]-3,3-dimethyl-7-oxo-4-thia-1-azabicyclo[3.2.0]heptane-2-carboxylic acid. The molecular weight of amoxicillin is 365.41. The empirical formula for amoxicillin is $C_{16}H_{19}N_3O_5S$ having a 52.59% carbon content, a 5.24% hydrogen content, a 11.50% nitrogen content, a 21.89% oxygen content, and a 8.77% sulfur content.

It is understood herein that the term cephalosporin derivative is a compound that contains the following chemical structural components: 3-[(acetyloxy)methyl]-7-[(R-)amino]-8-oxo-5-thia-1-azabicyclo[4.2.0]oct-2-ene-2-carboxylic acid, where R is a reactive group substituted on the nitrogen of the 7-amino group.

It is noted that for cephalosporin C there is a 5-amino-5-carboxy-1-oxopentyl group on the nitrogen of the 7-amino group. More specifically, for cephalosporin C, the "R" in the formula for cephalosporin derivatives is a 5-amino-5-carboxy-1-oxopentyl group.

It is noted that for cephalothin there is a 2-thienyl5-amino-5-carboxy-1-oxopentyl group on the nitrogen of the 7-amino group. More specifically, for cephalothin, the "R" in the formula for cephalosporin derivatives is a 5-amino-5-carboxy-1-oxopentyl group.

Specific suitable cephalosporin derivatives are as follows: cephalosporin C; cephalosporin C, sodium salt, dihydrate; cephalothin; cephalothin, sodium salt (also known as Averon-1, Cefalotin, Cephation, Ceporacin, Cepovenin, Chephalotin, Coaxin, Keflin, Lospoven, Microtin, Synclotin, and Toricelocin); cephapirin sodium; cefadroxil; cefazolin; cephalexin; cephalothin; cephapirin; cephradine; cefaclor; cefamandole; cefonicid; ceforanide; cefotetan (a cephamycin); cefoxitin (a cephamycin); ceftin; cefuroxime; the 1-acetyloxy ethyl ester of cefuroxime (cefuroxime axetil); cefoperazone; cefotaxime; ceftazidime; ceftizoxime; ceftriaxone; and moxalactam (a 1-oxa-beta-lactam).

In addition, analogs of cephalosporin are also suitable for topical treatment of acne. These cephalosporin analogs include: cephalosporin $P_1$; cephamycins; cepharanthine; and cephradine.

Suitable carriers for the form of ampicillin, amoxicillin, or other penicillin-like derivative or cephalosporin or cephalosporin derivative or cephalosporin analog can be selected from the group consisting of: a petrolatum vehicle; a water soluble gel; a mineral oil base; a blend of mineral oil and petrolatum; a suspension of an ion-exchange resin, e.g. Amberlite, in water; and other suitable pharmaceutical carriers, well known in the art.

By selection of a suitable vehicle, the ampicillin, amoxicillin, cephalosporin etc. can be administered topically as a solution, a gel, a lotion, a cream, or an ointment.

In addition to the form of ampicillin, amoxicillin, another aminopenicillin, or other penicillin-like derivative or cephalosporin or cephalosporin derivative or cephalosporin analog that is employed as an active ingredient, another active ingredient, such as benzoyl peroxide can be used.

For a topical formulation, in addition to the form of ampicillin, amoxicillin, another aminopenicillin, or other penicillin-like derivative, or cephalosporin or cephalosporin derivative or cephalosporin analog, the carrier, and possibly another active ingredient, the formulation can also include an agent which enhances penetration of an active ingredient through the skin. Exemplary agents which increase skin penetration are disclosed in the following U.S. patents all of which are incorporated herein by reference: U.S. Pat. No. 4,537,776 (a binary combination of N-(hydroxyethyl)-pyrrolidone and a cell-envelope disordering compound); U.S. Pat. No. 4,130,667 (using a sugar ester in combination with a sulfoxide or phosphine oxide); and U.S. Pat. No. 3,952,099 (using sucrose monooleate, decyl methyl sulfoxide, and alcohol).

Other exemplary materials that increase skin penetration are surfactants or wetting agents which include the following: polyoxyethylene sorbitan mono-oleoate (Polysorbate 80); sorbitan mono-oleate (Span 80); p-isooctyl polyoxyethylene-phenol polymer (Triton WR-1330); polyoxyethylene sorbitan tri-oleate (Tween 85); dioctyl sodium sulphosuccinate; and sodium sarcosinate (Sarcosyl NL-97); and other pharmaceutically acceptable surfactants.

Although there is not a complete understanding of the detailed theoretical mechanism upon which the efficacy of the topical dermatological compositions of the present invention which contain ampicillin, amoxicillin, another aminopenicillin, and other penicillin-like derivatives are founded, this lack of theoretical understanding in no way diminishes the benefits derived from employing the compositions and methods of the invention and in no way detracts from the utility of the invention as described herein.

Nevertheless, although not proven conclusively, it is felt that the topical use of ampicillin, amoxicillin, another aminopenicillin, and other penicillin-like derivatives or cephalosporin or cephalosporin derivative or cephalosporin analog of the invention help diminish the presence of *Proprionibacterium acnes*, and therefore diminish the effects on acne caused by the presence of *Proprionibacterium acnes*.

Furthermore, although not proven conclusively, it is felt that the topical use of ampicillin, amoxicillin, another aminopenicillin, and other penicillin-like derivatives or cephalosporin or cephalosporin derivative or cephalosporin analog of the invention serves to inhibit the skin's inflammatory response. More specifically, it is felt that by using the principles of the invention there is a decrease in chemotaxis of lymphocytes and neutrophils toward the pilosebaceous unit where inflammation and follicular plugging, and sebaceous fluid are accumulating. It may be that the major effect of topical ampicillin and amoxicillin is this anti-chemotactic effect of neutrophils and lymphocytes.

A variety of suitable compositions of the invention are presented below in Examples 1-82.

EXAMPLE 1

A topical dermatological composition containing ampicillin is obtained as follows.

Mix the following ingredients in the amounts specified.

| Ingredient | Weight Percent |
|---|---|
| Ethyl alcohol | 42.0 |
| Laureth-4 | 0.5 |
| Isopropyl alcohol | 6.0 |
| Ampicillin | 2.0 |
| Purified water | 49.5 |

Citric acid can be used to adjust the pH to a desired level.

The composition in Example 1 contains approximately 2% ampicillin.

Other suitable compositions can be made in accordance with Example 1 which include ampicillin in the following percentages: 0.5%, 1%, 3%, 4%, 5%, and 10%.

EXAMPLE 2

A topical dermatological composition containing amoxicillin is obtained as follows.

Mix the following ingredients in the amounts specified.

| Ingredient | Weight Percent |
|---|---|
| Ethyl alcohol | 42.0 |
| Laureth-4 | 0.5 |
| Isopropyl alcohol | 6.0 |
| Amoxicillin | 2.0 |
| Purified water | 49.5 |

Citric acid can be used to adjust the pH to a desired level.

The composition in Example 2 contains approximately 2% amoxicillin.

Other suitable compositions can be made in accordance with Example 2 which include amoxicillin in the following percentages: 0.5%, 1%, 3%, 4%, 5%, and 10%.

EXAMPLE 3

A topical dermatological composition containing ampicillin is obtained as follows.

Mix the following ingredients in the amounts specified.

| Ingredient | Weight Percent |
| --- | --- |
| Ethyl alcohol | 71.2 |
| Propylene glycol | 26.8 |
| Ampicillin | 2.0 |

The composition in Example 3 contains approximately 2% ampicillin.

EXAMPLE 4

A topical dermatological composition containing amoxicillin is obtained as follows.

Mix the following ingredients in the amounts specified.

| Ingredient | Weight Percent |
| --- | --- |
| Ethyl alcohol | 71.2 |
| Propylene glycol | 26.8 |
| Amoxicillin | 2.0 |

The composition in Example 4 contains approximately 2% amoxicillin.

Other suitable compositions can be made in accordance with Example 4 which include amoxicillin in the following percentages: 0.5%, 1%, 3%, 4%, 5%, and 10%.

Other topical dermatological compositions are presented below.

EXAMPLE 5

A formulation employing a water soluble gel as a carrier is obtained as follows. More details of the gel carrier are described in U.S. Pat. No. 4,837,378, incorporated herein by reference.

A 30 kilogram batch of a composition of the present invention containing ampicillin (as 0.75% by weight) is prepared as follows. 180 grams of Carbopol 940 (TM) (0.6% by weight of the final weight of the composition) is dissolved in 16.5 liters of distilled water containing 15 grams of ethylenediaminetetraacetic acid (EDTA) disodium dihydrate. Sufficient amount of 10 wt % sodium hydroxide (NaOH) solution is added to bring the pH value to about 5. This aqueous polymer solution is called "Part A". "Part B" is prepared by mixing 900 grams of propylene glycol (3% by weight of the final weight of the composition), 24 grams of methyl paraben (0.08% by weight of the final weight of the composition), and 6.0 grams of propyl paraben (0.02% by weight of the final weight of the composition). The mixture is added to 225 grams of ampicillin dispersed in 11.4 liters of distilled water maintained at 50 degrees Centigrade. Parts A and B are then mixed thoroughly and gelling of the composition results. A cold aqueous solution of NaOH is then used to adjust the final pH value to approximately 5.25. Distilled water is then added to give the desired 30 kilogram final weight. The NaOH and water are thoroughly mixed into a viscous gel.

Other suitable compositions can be made in accordance with Example 5 which include ampicillin in the following percentages: 0.5%, 1%, 2%, 3%, 4%, 5%, and 10%.

EXAMPLE 6

A formulation employing a water soluble gel as a carrier is obtained as follows. More details of the gel carrier are described in U.S. Pat. No. 4,837,378, incorporated herein by reference.

A 30 kilogram batch of a composition of the present invention containing amoxicillin (as 0.75% by weight) is prepared as follows. 180 grams of Carbopol 940 (TM) (0.6% by weight of the final weight of the composition) is dissolved in 16.5 liters of distilled water containing 15 grams of ethylenediaminetetraacetic acid (EDTA) disodium dihydrate. Sufficient amount of 10 wt % sodium hydroxide (NaOH) solution is added to bring the pH value to about 5. This aqueous polymer solution is called "Part A". "Part B" is prepared by mixing 900 grams of propylene glycol (3% by weight of the final weight of the composition), 24 grams of methyl paraben (0.08% by weight of the final weight of the composition), and 6.0 grams of propyl paraben (0.02% by weight of the final weight of the composition). The mixture is added to 225 grams of amoxicillin dispersed in 11.4 liters of distilled water maintained at 50 degrees Centigrade. Parts A and B are then mixed thoroughly and gelling of the composition results. A cold aqueous solution of NaOH is then used to adjust the final pH value to approximately 5.25. Distilled water is then added to give the desired 3 kilogram final weight. The NaOH and water are thoroughly mixed into a viscous gel.

Other suitable compositions can be made in accordance with Example 6 which include amoxicillin in the following percentages: 0.5%, 1%, 2%, 3%, 4%, 5%, and 10%.

EXAMPLE 7

Another topical dermatological gel is obtained by mixing the following ingredients in suitable amounts: allantoin, carbomer 934P, methylparaben, polyethylene glycol 400, propylene glycol, sodium hydroxide, purified water and ampicillin.

EXAMPLE 8

Another topical dermatological gel is obtained by mixing the following ingredients in suitable amounts: allantoin, carbomer 934P, methylparaben, polyethylene glycol 400, propylene glycol, sodium hydroxide, purified water and amoxicillin.

EXAMPLE 9

A dermatological lotion is obtained by mixing the following ingredients in the amounts specified:

| Ingredient | Weight Percent |
| --- | --- |
| Ethoxylated cetyl-stearyl alcohol | 7 |
| Cetyl alcohol | 0.75 |
| Isopropyl myristate | 5 |
| Butylated hydroxyanisole | 0.10 |

| Ingredient | Weight Percent |
| --- | --- |
| Polyoxyl 40 stearate | 0.25 |
| Water, deionized or distilled | 71.8 |
| Propylene glycol | 3 |
| Acetone | 10 |
| Dioctyl sodium sulphosuccinate | 0.1 |
| Ampicillin | 2 |

Other suitable composition can be made in accordance with Example 9 which include ampicillin in the following percentages: 0.5%, 1%, 3%, 4%, 5%, and 10%.

EXAMPLE 10

A dermatological lotion is obtained by mixing the following ingredients in the amounts specified:

| Ingredient | Weight Percent |
| --- | --- |
| Ethoxylated cetyl-stearyl alcohol | 7 |
| Cetyl alcohol | 0.75 |
| Isopropyl myristate | 5 |
| Butylated hydroxyanisole | 0.10 |
| Polyoxyl 40 stearate | 0.25 |
| Water, deionized or distilled | 71.8 |
| Propylene glycol | 3 |
| Acetone | 10 |
| Dioctyl sodium sulphosuccinate | 0.1 |
| Amoxicillin | 2 |

Other suitable compositions can be made in accordance with Example 10 which include amoxicillin in the following percentages: 0.5%, 1%, 3%, 4%, 5%, and 10%.

EXAMPLE 11

A powdery composition is obtained as follows. Mix the following ingredients in the amounts specified.

| Ingredient | Weight Percent |
| --- | --- |
| Benzoyl peroxide (micronized) | 1 to 35 |
| Calcium phosphate | 63 to 98.5 |
| Ampicillin | 0.5 to 5 |

EXAMPLE 12

A liquid composition is obtained as follows. Mix the following ingredients in the amounts specified.

| Ingredient | Weight Percent |
| --- | --- |
| Ampicillin | 0.5 to 5 |
| Benzoyl peroxide (micronized) | 1 to 30 |
| Ethanol | The Balance to 100% |

EXAMPLE 13

A topical dermatological composition containing ampicillin is obtained as follows.
Mix the following ingredients in the amounts specified.

| Ingredient | Weight Percent |
| --- | --- |
| Ethyl alcohol | 44.0 |
| Laureth-4 | 0.5 |
| Isopropyl alcohol | 6.0 |
| Ampicillin | 2.0 |

| Ingredient | Weight Percent |
| --- | --- |
| Purified water | 49.5 |

Citric acid can be used to adjust the pH to a desired level.

The composition in Example 13 contains approximately 2% ampicillin.

Other suitable compositions can be made in accordance with Example 13 which include ampicillin in the following percentages: 0.5%, 1%, 3%, 5%, and 10%.

EXAMPLE 14

A lotion composition is obtained as follows. Mix the following ingredients in the amounts specified.

| Ingredient | Weight Percent |
| --- | --- |
| Ethoxylated cetyl-stearyl alcohol | 7 |
| Cetyl alcohol | 0.75 |
| Isopropyl myristate | 5 |
| Butylated hydroxyanisole | 0.10 |
| Polyoxyl 40 stearate | 0.25 |
| Water, deionized or distilled | 66.8 |
| Propylene glycol | 3 |
| Benzoyl peroxide (micronized) | 5 |
| Acetone | 10 |
| Dioctyl sodium sulphosuccinate | 0.1 |
| Ampicillin | 2 |

Other suitable compositions can be made in accordance with Example 14 which include ampicillin in the following percentages: 0.5%, 1%, 3%, 4%, 5%, and 10%.

EXAMPLE 15

A cream composition is obtained as follows. Mix the following ingredients in the amounts specified.

| Ingredient | Weight Percent |
| --- | --- |
| Ethoxylated cetyl-stearyl alcohol | 15 |
| Cetyl alcohol | 1.25 |
| Isopropyl myristate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| Ampicillin | 3 |

Other suitable compositions can be made in accordance with Example 15 which include ampicillin in the following percentages: 0.5%, 1%, 2%, 4%, 5%, and 10%.

EXAMPLE 16

A gel composition is obtained as follows. Mix the following ingredients in the amounts specified.

| Ingredient | Weight Percent |
| --- | --- |
| Water, deionized or distilled | 51.65 |
| Butylated hydroxyanisole | 0.10 |
| Benzoyl peroxide (micronized) | 5 |
| Dioctyl sodium sulphosuccinate | 1 |
| Colloidal Bentonite | 2.5 |
| Carboxy vinyl polymer (acid form) | 1 |
| Ethyl alcohol | 35 |

-continued

| Ingredient | Weight Percent |
| --- | --- |
| Diisopropanolamine | 0.75 |
| Ampicillin | 3 |

Other suitable compositions can be made in accordance with Example 16 which include ampicillin in the following percentages: 0.5%, 1%, 2%, 4%, 5%, and 10%.

EXAMPLE 17

A suspension composition is obtained as follows. Mix the following ingredients in the amounts specified.

| Ingredient | Weight Percent |
| --- | --- |
| Water, deionized or distilled | 54.97 |
| Butylated hydroxyanisole | 0.10 |
| Benzoyl peroxide (micronized) | 5 |
| Dioctyl sodium sulphosuccinate | 1 |
| Colloidal Bentonite | 1.5 |
| Carboxy vinyl polymer (acid form) | 0.25 |
| Ethyl alcohol | 35 |
| Diisopropanolamine | 0.18 |
| Ampicillin | 2 |

Other suitable compositions can be made in accordance with Example 17 which include ampicillin in the following percentages: 0.5%, 1%, 3%, 4%, 5%, and 10%.

EXAMPLE 18

A powdery composition is obtained as follows. Mix the following ingredients in the amounts specified.

| Ingredient | Weight Percent |
| --- | --- |
| Benzoyl peroxide (micronized) | 1 to 35 |
| Calcium phosphate | 63 to 98.5 |
| Amoxicillin | 0.5 to 5 |

EXAMPLE 19

A liquid composition is obtained as follows. Mix the following ingredient in the amounts specified.

| Ingredient | Weight Percent |
| --- | --- |
| Amoxicillin | 0.5 to 5 |
| Benzoyl peroxide (micronized) | 1 to 30 |
| Ethanol | The Balance to 100% |

EXAMPLE 20

A lotion composition is obtained as follows. Mix the following ingredients in the amounts specified.

| Ingredient | Weight Percent |
| --- | --- |
| Ethoxylated cetyl-stearyl alcohol | 7 |
| Cetyl alcohol | 0.75 |
| Isopropyl myristate | 5 |
| Butylated hydroxyanisole | 0.10 |
| Polyoxyl 40 stearate | 0.25 |
| Water, deionized or distilled | 66.8 |
| Propylene glycol | 3 |
| Benzoyl peroxide (micronized) | 5 |
| Acetone | 10 |
| Dioctyl sodium sulphosuccinate | 0.1 |
| Amoxicillin | 2 |

Other suitable compositions can be made in accordance with Example 20 which include amoxicillin in the following percentages: 0.5%, 1%, 3%, 4%, 5%, and 10%.

EXAMPLE 21

A cream composition is obtained as follows. Mix the following ingredients in the amounts specified.

| Ingredient | Weight Percent |
| --- | --- |
| Ethoxylated cetyl-stearyl alcohol | 15 |
| Cetyl alcohol | 1.25 |
| Isopropyl myristate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| Amoxicillin | 3 |

Other suitable compositions can be made in accordance with Example 21 which include amoxicillin in the following percentages: 0.5%, 1%, 2%, 4%, 5%, and 10%.

EXAMPLE 22

A gel composition is obtained as follows. Mix the following ingredients in the amounts specified.

| Ingredient | Weight Percent |
| --- | --- |
| Water, deionized or distilled | 51.65 |
| Butylated hydroxyanisole | 0.10 |
| Benzoyl peroxide (micronized) | 5 |
| Dioctyl sodium sulphosuccinate | 1 |
| Colloidal Bentonite | 2.5 |
| Carboxy vinyl polymer (acid form) | 1 |
| Ethyl alcohol | 35 |
| Diisopropanolamine | 0.75 |
| Amoxicillin | 3 |

Other suitable compositions can be made in accordance with Example 22 which include amoxicillin in the following percentages: 0.5%, 1%, 2%, 4%, 5%, and 10%.

EXAMPLE 23

A suspension composition is obtained as follows. Mix the following ingredients in the amounts specified.

| Ingredient | Weight Percent |
| --- | --- |
| Water, deionized or distilled | 54.97 |
| Butylated hydroxyanisole | 0.10 |
| Benzoyl peroxide (micronized) | 5 |
| Dioctyl sodium sulphosuccinate | 1 |
| Colloidal Bentonite | 1.5 |
| Carboxy vinyl polymer (acid form) | 0.25 |
| Ethyl alcohol | 35 |
| Diisopropanolamine | 0.18 |
| Amoxicillin | 2 |

Other suitable compositions can be made in accordance with Example 23 which include amoxicillin in the following percentages: 0.5%, 1%, 3%, 4%, 5%, and 10%.

EXAMPLE 24

An oil-in-water emulsion containing ampicillin in ointment form is obtained as follows.

Part A is comprised of a 3.33% aqueous solution of ampicillin.

Part B is an ointment base comprised of:

| Ingredient | Weight Percent |
|---|---|
| viscid paraffin | 35 |
| white vaseline | 35 |
| cetylstearyl alcohol | 30 |

A mixture is obtained as follows. Mix 60 ml. of Part A is mixed with 40 ml. of Part B to provide an oil-in-water emulsion in ointment form containing approximately 2% ampicillin.

Other suitable compositions can be made in accordance with Example 24 which include ampicillin in the following percentages: 0.5%, 1%, 3%, 4%, 5%, and 10%.

EXAMPLE 25

A mineral-oil-based ampicillin ointment is obtained as follows.

Part A is comprised of a 6.66% aqueous solution of ampicillin.

Part B is an ointment base comprised of:

| Ingredient | Parts |
|---|---|
| glycerin | 5 |
| isopropyl alcohol, 96% | 5 |
| mineral oil | 60 |

A mixture is obtained as follows. Mix 30 ml. of Part A with 70 ml. of Part B to provide a mineral-oil-based ointment containing approximately 2% ampicillin.

Other suitable compositions can be made in accordance with Example 25 which include ampicillin in the following percentages: 0.5%, 1%, 3%, 4%, 5%, and 10%.

From the volumes in this Example, it is easy to convert to approximate weight percents. To make the conversion, certain inherent properties of water, isopropyl alcohol, glycerin, and mineral oil are employed. More specifically, to make the conversion to approximate weight percents, the known densities of water, isopropyl alcohol, glycerin, and mineral oil are employed. The known density of water is approximately 1 g/ml. The known density of isopropyl alcohol is approximately 0.78 g/ml. The known density of glycerin is approximately 1.25 g/ml. The known density of mineral oil is approximately 0.85 g/ml.

The weight of the 30 ml. of part A is approximately 30 grams, in view of the fact that part A is predominately water. By taking 30 ml. of part A, approximately 2 grams of antibiotic (30 g. × 6.66%) and approximately 28 grams of water (30 g. × 93.34%) are obtained.

By taking 70 ml. of part B, approximately 3.9 grams of isopropyl alcohol (5 ml. × 0.78 g/ml.), approximately 6.25 grams of glycerin (5 ml. × 1.25 g/ml.), and approximately 51 grams of mineral oil (60 ml. × 0.85 g/ml.) are obtained. The weight of 70 ml. of part B is approximately 61.15 grams (3.9 g. + 6.25 g. + 51 g.).

Therefore, the total weight of parts A and B combined is approximately 91.15 grams (30 g. + 61.15 g.).

In the combination of parts A and B, the weight percents of the individual carrier components are as approximately as follows: water, 31%; isopropyl alcohol, 4.3%; glycerin, 6.86%; and mineral oil, 55.95%. It is noted that the combined weight percentages of the water-miscible alcohols is approximately 11.2% (4.3% + 6.86%). It is also noted that the combined weight percentages of the water and water-miscible alcohols is approximately 42.2% (31% + 11.2%).

EXAMPLE 26

A topical dermatological composition containing cephalosporin C is obtained as follows.

Mix the following ingredients in the amounts specified.

| Ingredient | Weight Percent |
|---|---|
| Ethyl alcohol | 44.0 |
| Laureth-4 | 0.5 |
| Isopropyl alcohol | 6.0 |
| Cephalosporin C | 1.0 |
| Purified water | balance |

Citric acid can be used to adjust the pH to a desired level.

The composition in Example 26 contains approximately 1% Cephalosporin C.

Other suitable compositions can be made in accordance with Example 26 which include Cephalosporin C in the following percentages: 0.5%, 2%, 3%, 4%, 5%, and 10%.

EXAMPLE 27

A topical dermatological composition containing cephalosporin C is obtained as follows.

Mix the following ingredients in the amounts specified.

| Ingredient | Weight Percent |
|---|---|
| Ethyl alcohol | 71.2 |
| Propylene glycol | 26.8 |
| Cephalosporin C | 2.0 |

The composition in Example 27 contains approximately 2% cephalosporin C.

Other topical dermatological compositions are presented below.

EXAMPLE 28

A formulation employing a water soluble gel as a carrier is obtained as follows. More details of the gel carrier are described in U.S. Pat. No. 4,837,378, incorporated herein by reference.

A 30 kilogram batch of a composition of the present invention containing cephalosporin C (as 0.75% by weight) is prepared as follows. 180 grams of Carbopol 940 (TM) (0.6% by weight of the final weight of the composition) is dissolved in 16.5 liters of distilled water containing 15 grams of ethylenediaminetetraacetic acid (EDTA) disodium dihydrate. Sufficient amount of 10 wt % sodium hydroxide (NaOH) solution is added to bring the pH value to about 5. This aqueous polymer solution is called "Part A". "Part B" is prepared by mixing 900 grams of propylene glycol (3% by weight of the final weight of the composition), 24 grams of methyl paraben (0.08% by weight of the final weight of the composition), and 6.0 grams of propyl paraben (0.02% by weight of the final weight of the composition). The mixture is added to 225 grams of cephalosporin C dispersed in 11.4 liters of distilled water maintained at 50 degrees Centigrade. Parts A and B are then mixed thoroughly and gelling of the composition results. A cold aqueous solution of NaOH is then used to adjust the final pH value to approximately 5.25. Distilled water is then added to give the desired 30 kilogram final weight. The NaOH and water are thoroughly mixed into a viscous gel.

Other suitable compositions can be made in accordance with Example 28 which include cephalosporin C in the following percentages: 0.5%, 1%, 2%, 3%, 4%, 5%, and 10%.

EXAMPLE 29

Another topical dermatological gel is obtained by mixing the following ingredients in suitable amounts: allantoin, carbomer 934P, methylparaben, polyethylene glycol 400, propylene glycol, sodium hydroxide, purified water and cephalosporin C.

EXAMPLE 30

A dermatological lotion containing ampicillin is obtained by mixing the following ingredients in the amounts specified. The ingredients in Container A are blended with the ingredients in Container B.

| Ingredient | Weight Percent of ingredient in overall lotion |
| --- | --- |
| In Container A: | |
| Ethoxylated cetyl-stearyl alcohol | 7.00 |
| Cetyl alcohol | 0.75 |
| Isopropyl myristate | 5.00 |
| Butylated hydroxyanisole | 0.10 |
| Polyoxyl 40 stearate | 0.25 |
| Water, deionized or distilled | 70.80 |
| Propylene glycol | 3.00 |
| Acetone | 7.00 |
| Dioctyl sodium sulfosuccinate | 0.10 |
| In Container B: | |
| Acetone | 3.00 |
| ampicillin | 3.00 |

Citric acid can be used to adjust the pH to a desired level.

To obtain the lotion composition in Example 30, the composition in Container A is prepared. This composition in Container A is stable for long periods of time.

Container B can contain only ampicillin for a long period of time. Just prior to forming the complete location composition, 3 grams of acetone are added to Container B to dissolve the ampicillin. Then, the contents of Container A and Container B are combined to form the complete lotion composition of the invention.

The composition in Example 30 contains approximately 3% ampicillin.

Other suitable compositions can be made in accordance with Example 30 which include ampicillin in the following percentages: 0.5%, 1%, 2%, 4%, 5%, and 10%.

EXAMPLE 31

A powdery composition is obtained as follows. Mix the following ingredients in the amounts specified.

| Ingredient | Weight Percent |
| --- | --- |
| Benzoyl peroxide (micronized) | 1 to 35 |
| Calcium phosphate | 63 to 98.5 |
| Cephalosporin C | 0.5 to 5 |

EXAMPLE 32

A liquid composition is obtained as follows. Mix the following ingredients in the amounts specified.

| Ingredient | Weight Percent |
| --- | --- |
| Cephalosporin C | 0.5 to 5 |
| Benzoyl peroxide (micronized) | 1 to 30 |
| Ethanol | The Balance to 100% |

EXAMPLE 33

A lotion composition is obtained as follows. Mix the following ingredients in the amounts specified.

| Ingredient | Weight Percent |
| --- | --- |
| Ethoxylated cetyl-stearyl alcohol | 7 |
| Cetyl alcohol | 0.75 |
| Isopropyl myristate | 5 |
| Butylated hydroxyanisole | 0.10 |
| Polyoxyl 40 stearate | 0.25 |
| Water, deionized or distilled | 66.8 |
| Propylene glycol | 3 |
| Benzoyl peroxide (micronized) | 5 |
| Acetone | 10 |
| Dioctyl sodium sulphosuccinate | 0.1 |
| Cephalosporin C | 2 |

Other suitable compositions can be made in accordance with Example 33 which include cephalosporin C in the following percentages: 0.5%, 1%, 3%, 4%, 5%, and 10%.

EXAMPLE 34

A cream composition is obtained as follows. Mix the following ingredients in the amounts specified.

| Ingredient | Weight Percent |
| --- | --- |
| Ethoxylated cetyl-stearyl alcohol | 15 |
| Cetyl alcohol | 1.25 |
| Isopropyl myristate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| Cephalosporin C | 3 |

Other suitable compositions can be made in accordance with Example 34 which include cephalosporin C in the following percentages: 0.5%, 1%, 2%, 4%, 5%, and 10%.

EXAMPLE 35

A gel composition is obtained as follows. Mix the following ingredients in the amounts specified.

| Ingredient | Weight Percent |
| --- | --- |
| Water, deionized or distilled | 51.65 |

-continued

| Ingredient | Weight Percent |
| --- | --- |
| Butylated hydroxyanisole | 0.10 |
| Benzoyl peroxide (micronized) | 5 |
| Dioctyl sodium sulphosuccinate | 1 |
| Colloidal Bentonite | 2.5 |
| Carboxy vinyl polymer (acid form) | 1 |
| Ethyl alcohol | 35 |
| Diisopropanolamine | 0.75 |
| Cephalosporin C | 3 |

Other suitable compositions can be made in accordance with Example 35 which include cephalosporin C in the following percentages: 0.5%, 1%, 2%, 4%, 5%, and 10%.

EXAMPLE 36

A suspension composition is obtained as follows. Mix the following ingredients in the amounts specified.

| Ingredient | Weight Percent |
| --- | --- |
| Water, deionized or distilled | 54.97 |
| Butylated hydroxyanisole | 0.10 |
| Benzoyl peroxide (micronized) | 5 |
| Dioctyl sodium sulphosuccinate | 1 |
| Colloidal Bentonite | 1.5 |
| Carboxy vinyl polymer (acid form) | 0.25 |
| Ethyl alcohol | 35 |
| Diisopropanolamine | 0.18 |
| Cephalosporin C | 2 |

Other suitable compositions can be made in accordance with Example 36 which include cephalosporin C in the following percentages: 0.5%, 1%, 3%, 4%, 5%, and 10%.

EXAMPLE 37

A topical dermatological composition containing amoxicillin is obtained as follows.

Mix the following ingredients in the amounts specified.

| Ingredient | Weight Percent |
| --- | --- |
| Ethyl alcohol | 44.0 |
| Laureth-4 | 0.5 |
| Isopropyl alcohol | 6.0 |
| Amoxicillin | 2.0 |
| Purified water | 49.5 |

Citric acid can be used to adjust the pH to a desired level.

The composition in Example 37 contains approximately 2% amoxicillin.

Other suitable compositions can be made in accordance with Example 37 which include amoxicillin in the following percentages: 0.5%, 1%, 3%, 4%, 5%, and 10%.

EXAMPLE 38

A topical dermatological composition containing ceftin is obtained as follows.

Mix the following ingredients in the amounts specified.

| Ingredient | Weight Percent |
| --- | --- |
| Ethyl alcohol | 44.0 |
| Laureth-4 | 0.5 |
| Isopropyl alcohol | 6.0 |
| Ceftin | 1.0 |
| Purified water | balance |

Citric acid can be used to adjust the pH to a desired level.

The composition in Example 38 contains approximately 1% Ceftin.

Other suitable compositions can be made in accordance with Example 38 which include Ceftin in the following percentages: 0.5%, 2%, 3%, 4%, 5%, and 10%. Example 37

EXAMPLE 39

A dermatological lotion is obtained by mixing the following ingredients in suitable amounts: ampicillin (approximately 1% by weight); and a carrier which includes isopropyl alcohol (approximately 80% by weight), purified water (approximately 9% by weight), and propylene glycol (approximately 10% by weight).

EXAMPLE 40

A dermatological lotion is obtained by mixing the following ingredients in suitable amounts: amoxicillin (approximately 1% by weight); and a carrier which includes isopropyl alcohol (approximately 80% by weight), purified water (approximately 9% by weight), and propylene glycol (approximately 10% by weight).

EXAMPLE 41

A dermatological lotion is obtained by mixing the following ingredients in suitable amounts: cephalosporin C (approximately 1% by weight); and a carrier which includes isopropyl alcohol (approximately 80% by weight), purified water (approximately 9% by weight), and propylene glycol (approximately 10% by weight).

EXAMPLE 42

A topical dermatological composition containing cephalexin is obtained as follows.

Mix the following ingredients in the amounts specified.

| Ingredient | Weight Percent |
| --- | --- |
| Ethyl alcohol | 42.0 |
| Laureth-4 | 0.5 |
| Isopropyl alcohol | 6.0 |
| Cephalexin | 1.0 |
| Purified water | balance |

Citric acid can be used to adjust the pH to a desired level.

The composition in Example 42 contains approximately 1% Cephalexin.

Other suitable compositions can be made in accordance with Example 42 which include Cephalexin in the following percentages: 0.5%, 2%, 3%, 4%, 5%, and 10%.

EXAMPLE 43

A topical dermatological composition containing cephalexin is obtained as follows.

Mix the following ingredients in the amounts specified.

| Ingredient | Weight Percent |
| --- | --- |
| Ethyl alcohol | 48.0 |
| Laureth-4 | 0.5 |
| Isopropyl alcohol | 4.0 |
| Propylene glycol | 10.0 |
| Cephalexin | 1.0 |
| Purified water | balance |

Citric acid can be used to adjust the pH to a desired level.

The composition in Example 43 contains approximately 1% Cephalexin.

Other suitable compositions can be made in accordance with Example 43 which include Cephalexin in the following percentages: 0.5%, 2%, 3%, 4%, 5%, and 10%.

EXAMPLE 44

A topical dermatological composition containing Cephalexin is obtained as follows.

Mix the following ingredients in the amounts specified.

| Ingredient | Weight Percent |
| --- | --- |
| Ethyl alcohol | 44.0 |
| Laureth-4 | 0.5 |
| Isopropyl alcohol | 6.0 |
| Cephalexin | 1.0 |
| Purified water | balance |

Citric acid can be used to adjust the pH to a desired level.

The composition in Example 44 contains approximately 1% Cephalexin.

Other suitable compositions can be made in accordance with Example 44 which include Cephalexin in the following percentages: 0.5%, 2%, 3%, 4%, 5%, and 10%.

EXAMPLE 45

A topical dermatological composition containing cephalexin is obtained as follows.

Mix the following ingredients in the amounts specified.

| Ingredient | Weight Percent |
| --- | --- |
| Ethyl alcohol | 48.0 |
| Laureth-4 | 0.5 |
| Isopropyl alcohol | 4.0 |
| Propylene glycol | 10.0 |
| Cephalexin | 1.0 |
| Purified water | balance |

Citric acid can be used to adjust the pH to a desired level.

The composition in Example 45 contains approximately 1% Cephalexin.

Other suitable compositions can be made in accordance with Example 45 which include Cephalexin in the following percentages: 0.5%, 2%, 3%, 4%, 5%, and 10%.

EXAMPLE 46

A topical dermatological composition containing cefaclor is obtained as follows.

Mix the following ingredients in the amounts specified.

| Ingredient | Weight Percent |
| --- | --- |
| Ethyl alcohol | 44.0 |
| Laureth-4 | 0.5 |
| Isopropyl alcohol | 6.0 |
| Cefaclor | 2.0 |
| Purified water | balance |

Citric acid can be used to adjust the pH to a desired level.

The composition in Example 46 contains approximately 2% Cefaclor.

Other suitable compositions can be made in accordance with Example 46 which include Cefaclor in the following percentages: 0.5%, 1%, 3%, 4%, 5%, and 10%.

EXAMPLE 47

A topical dermatological composition containing cefaclor is obtained as follows.

Mix the following ingredients in the amounts specified.

| Ingredient | Weight Percent |
| --- | --- |
| Ethyl alcohol | 48.0 |
| Laureth-4 | 0.5 |
| Isopropyl alcohol | 4.0 |
| Propylene glycol | 10.0 |
| Cefaclor | 1.0 |
| Purified water | balance |

Citric acid can be used to adjust the pH to a desired level.

The composition in Example 47 contains approximately 1% Cefaclor.

Other suitable compositions can be made in accordance with Example 47 which include Cefaclor in the following percentages: 0.5%, 2%, 3%, 4%, 5%, and 10%.

EXAMPLE 48

A topical dermatological composition containing cefuroxime is obtained as follows.

Mix the following ingredients in the amounts specified.

| Ingredient | Weight Percent |
| --- | --- |
| Ethyl alcohol | 44.0 |
| Laureth-4 | 0.5 |
| Isopropyl alcohol | 6.0 |
| Cefuroxime | 1.0 |
| Purified water | balance |

Citric acid can be used to adjust the pH to a desired level.

The composition in Example 48 contains approximately 1% Cefuroxime.

Other suitable compositions can be made in accordance with Example 48 which include Cefuroxime in the following percentages: 0.5%, 2%, 3%, 4%, 5%, and 10%.

EXAMPLE 49

A topical dermatological composition containing cefuroxime is obtained as follows.

Mix the following ingredients in the amounts specified.

| Ingredient | Weight Percent |
| --- | --- |
| Ethyl alcohol | 48.0 |
| Laureth-4 | 0.5 |
| Isopropyl alcohol | 4.0 |
| Propylene glycol | 10.0 |
| Cefuroxime | 1.0 |
| Purified water | balance |

Citric acid can be used to adjust the pH to a desired level.

The composition in Example 49 contains approximately 1% Cefuroxime.

Other suitable compositions can be made in accordance with Example 49 which include Cefuroxime in the following percentages: 0.5%, 2%, 3%, 4%, 5%, and 10%.

EXAMPLE 50

A topical dermatological composition containing cefuroxime axetil is obtained as follows. It is noted that cefuroxime axetil is th 1-acetyloxy ethyl ester of cefuroxime.

Mix the following ingredients in the amounts specified.

| Ingredient | Weight Percent |
| --- | --- |
| Ethyl alcohol | 44.0 |
| Laureth-4 | 0.5 |
| Isopropyl alcohol | 6.0 |
| Cefuroxime axetil | 1.0 |
| Purified water | balance |

Citric acid can be used to adjust the pH to a desired level.

The composition in Example 50 contains approximately 1% Cefuroxime axetil.

Other suitable compositions can be made in accordance with Example 50 which include Cefuroxime axetil in the following percentages: 0.5%, 2%, 3%, 4%, 5%, and 10%.

EXAMPLE 51

A topical dermatological composition containing cefuroxime axetil is obtained as follows. Mix the following ingredients in the amounts specified.

| Ingredient | Weight Percent |
| --- | --- |
| Ethyl alcohol | 48.0 |
| Laureth-4 | 0.5 |
| Isopropyl alcohol | 4.0 |
| Propylene glycol | 10.0 |
| Cefuroxime axetil | 1.0 |
| Purified water | balance |

Citric acid can be used to adjust the pH to a desired level.

The composition in Example 51 contains approximately 1% Cefuroxime axetil.

Other suitable compositions can be made in accordance with Example 51 which include Cefuroxime axetil in the following percentages: 0.5%, 2%, 3%, 4%, 5%, and 10%.

EXAMPLE 52

A topical dermatological composition containing cefoperazone is obtained as follows.

Mix the following ingredients in the amounts specified.

| Ingredient | Weight Percent |
| --- | --- |
| Ethyl alcohol | 44.0 |
| Laureth-4 | 0.5 |
| Isopropyl alcohol | 6.0 |
| Cefoperazone | 1.0 |
| Purified water | balance |

Citric acid can be used to adjust the pH to a desired level.

The composition in Example 52 contains approximately 1% Cefoperazone.

Other suitable compositions can be made in accordance with Example 52 which include Cefoperazone in the following percentages: 0.5%, 2%, 3%, 4%, 5%, and 10%.

EXAMPLE 53

A topical dermatological composition containing cefoperazone is obtained as follows.

Mix the following ingredients in the amounts specified.

| Ingredient | Weight Percent |
| --- | --- |
| Ethyl alcohol | 48.0 |
| Laureth-4 | 0.5 |
| Isopropyl alcohol | 4.0 |
| Propylene glycol | 10.0 |
| Cefoperazone | 1.0 |
| Purified water | balance |

Citric acid can be used to adjust the pH to a desired level.

The composition in Example 53 contains approximately 1% Cefoperazone.

Other suitable compositions can be made in accordance with Example 53 which include Cefoperazone in the following percentages: 0.5%, 2%, 3%, 4%, 5%, and 10%.

EXAMPLE 54

A topical dermatological composition containing ampicillin is obtained as follows.

| Ingredient | Weight Percent |
| --- | --- |
| Ethyl alcohol | 48.0 |
| Laureth-4 | 0.5 |
| Isopropyl alcohol | 4.0 |
| Propylene glycol | 10.0 |
| Ampicillin | 1.0 |
| Purified water | balance |

Mix the following ingredients in the amounts specified.

Citric acid can be used to adjust the pH to a desired level.

The composition in Example 54 contains approximately 1% Ampicillin.

Other suitable compositions can be made in accordance with Example 54 which include Ampicillin in the following percentages: 0.5%, 2%, 3%, 4%, 5%, and 10%.

EXAMPLE 55

A topical dermatological composition containing amoxicillin is obtained as follows.

Mix the following ingredients in the amounts specified.

| Ingredient | Weight Percent |
| --- | --- |
| Ethyl alcohol | 48.0 |
| Laureth-4 | 0.5 |
| Isopropyl alcohol | 4.0 |
| Propylene glycol | 10.0 |
| Amoxicillin | 1.0 |
| Purified water | balance |

Citric acid can be used to adjust the pH to a desired level.

The composition in Example 55 contains approximately 1% Amoxicillin.

Other suitable compositions can be made in accordance with Example 55 which include Amoxicillin in the following percentages: 0.5%, 2%, 3%, 4%, 5%, and 10%.

EXAMPLE 56

A topical dermatological composition containing ceftin is obtained as follows.

Mix the following ingredients in the amounts specified.

| Ingredient | Weight Percent |
| --- | --- |
| Ethyl alcohol | 44.0 |
| Laureth-4 | 0.5 |
| Isopropyl alcohol | 6.0 |
| Ceftin | 1.0 |
| Purified water | balance |

Citric acid can be used to adjust the pH to a desired level.

The composition in Example 56 contains approximately 1% Ceftin.

Other suitable compositions can be made in accordance with Example 56 which include Ceftin in the following percentages: 0.5%, 2%, 3%, 4%, 5%, and 10%.

EXAMPLE 57

A topical dermatological composition containing ceftin is obtained as follows.

Mix the following ingredients in the amounts specified.

| Ingredient | Weight Percent |
| --- | --- |
| Ethyl alcohol | 48.0 |
| Laureth-4 | 0.5 |
| Isopropyl alcohol | 4.0 |
| Propylene glycol | 10.0 |
| Ceftin | 1.0 |
| Purified water | balance |

Citric acid can be used to adjust the pH to a desired level.

The composition in Example 57 contains approximately 1% Ceftin.

Other suitable compositions can be made in accordance with Example 57 which include Ceftin in the following percentages: 0.5%, 2%, 3%, 4%, 5%, and 10%.

For Examples 58-60, reference is made to U.S. Pat. No. 4,497,794, incorporated herein by reference, in which topical gel compositions containing the antibiotic erythromycin and benzoyl peroxide in a gel carrier are disclosed. A number of topical gel compositions of the present invention can be made by simply replacing the erythromycin disclosed in the gel compositions in said patent with ampicillin, amoxicillin, or cephalosporin C, respectively, to provide topical gel compositions of the invention which contain benzoyl peroxide and the respective antibiotic of the invention.

The gel carrier or vehicle for Examples 58-60, prior to addition of the benzoyl peroxide and prior to addition of the respective antibiotic of the invention and, as explained below, the approximately 3 ml. of ethyl alcohol used to dissolve the respective antibiotic for addition to the gel carrier to which benzoyl peroxide has been added, is comprised of the following ingredients in the approximate amounts specified.

| Ingredient in gel carrier | Weight Percent in the Final Mixture containing antibiotic, benzoyl peroxide, and gel carrier |
| --- | --- |
| Butylated hydroxyanisole | 0.10 |
| Colloidal Bentonite | 2.50 |
| Carboxy vinyl polymer (acid form) | 1.00 |
| Water, deionized or distilled | 54.65 |
| Diisopropanolamine | 0.75 |
| Ethyl alcohol | 32.00 |
| Dioctyl sodium sulfosuccinate | 1.00 |

EXAMPLE 58

A topical dermatological gel composition containing ampicillin antibiotic and benzoyl peroxide in a gel carrier or vehicle is obtained as follows.

To a first container add the benzoyl peroxide and the gel carrier or vehicle ingredients (approximately 5 grams of benzoyl peroxide and approximately 89 grams of gel carrier or vehicle). To a second container add powdered ampicillin (approximately 3 grams of ampicillin). The contents of the first container and the contents of the second container are stable for long periods of time. When the topical composition containing ampicillin and benzoyl peroxide of the invention is to be made, a quantity of 70% ethyl alcohol (e.g. 3 ml.) is added to the second container to dissolve the ampicillin and form an alcoholic solution thereof. Then the alcoholic solution of ampicillin is added to the first container, and all the ingredients are mixed to form the topical gel composition of the invention which contains both ampicillin and benzoyl peroxide. This composition of the invention is stable, under refrigeration, for approximately 3 months.

More specifically, the blended topical gel composition of the invention with contains ampicillin and benzoyl peroxide in a gel carrier or vehicle has the following components in the approximate amounts specified.

| Ingredient | Weight Percent |
| --- | --- |
| ampicillin | 3.0 |
| Benzoyl peroxide | 5.0 |
| Gel carrier or vehicle | 92.0 |

Citric acid can be used to adjust the pH to a desired level.

The composition in Example 58 contains approximately 3% ampicillin.

Other suitable compositions can be made in accordance with Example 58 which include ampicillin in the following percentages: 0.5%, 1%, 2%, 4%, 5%, and 10%.

EXAMPLE 59

A topical dermatological gel composition containing amoxicillin antibiotic and benzoyl peroxide in a gel carrier or vehicle is obtained as follows.

To a first container add the benzoyl peroxide and the gel carrier or vehicle ingredients (approximately 5 grams of benzoyl peroxide and approximately 89 grams of gel carrier or vehicle). To a second container add powdered amoxicillin (approximately 3 grams of amoxicillin). The contents of the first container and the contents of the second container are stable for long periods of time. When the topical composition containing amoxicillin and benzoyl peroxide of the invention is to be made, a quantity of 70% ethyl alcohol (e.g. 3 ml.) is added to the second container to dissolve the amoxicillin and form an alcoholic solution thereof. Then the alcoholic solution of amoxicillin is added to the first container, and all the ingredients are mixed to form the topical gel composition of the invention which contains both amoxicillin and benzoyl peroxide. This composition of the invention is stable, under refrigeration, for approximately 3 months.

More specifically, the blended topical gel composition of the invention with contains amoxicillin and benzoyl peroxide in a gel carrier or vehicle has the following components in the approximate amounts specified.

| Ingredient | Weight Percent |
| --- | --- |
| amoxicillin | 3.0 |
| Benzoyl peroxide | 5.0 |
| Gel carrier or vehicle | 92.0 |

Citric acid can be used to adjust the pH to a desired level.

The composition in Example 59 contains approximately 3% amoxicillin.

Other suitable compositions can be made in accordance with Example 59 which include amoxicillin in the following percentages: 0.5%, 1%, 2%, 4%, 5%, and 10%.

EXAMPLE 60

A topical dermatological gel composition containing cephalosporin C antibiotic and benzoyl peroxide in a gel carrier or vehicle is obtained as follows.

To a first container add the benzoyl peroxide and the gel carrier or vehicle ingredients (approximately 5 grams of benzoyl peroxide and approximately 89 grams of gel carrier or vehicle). To a second container add powdered cephalosporin C (approximately 3 grams of cephalosporin C). The contents of the first container and the contents of the second container are stable for long periods of time. When the topical composition containing cephalosporin C and benzoyl peroxide of the invention is to be made, a quantity of 70% ethyl alcohol (e.g. 3 ml.) is added to the second container to dissolve the cephalosporin C and form an alcoholic solution thereof. Then the alcoholic solution of cephalosporin C is added to the first container, and all the ingredients are mixed to form the topical gel composition of the invention which contains both cephalosporin C and benzoyl peroxide. This composition of the invention is stable, under refrigeration, for approximately 3 months.

More specifically, the blended topical gel composition of the invention with contains cephalosporin C and benzoyl peroxide in a gel carrier or vehicle has the following components in the approximate amounts specified.

| Ingredient | Weight Percent |
| --- | --- |
| cephalosporin C | 3.0 |
| Benzoyl peroxide | 5.0 |
| Gel carrier or vehicle | 92.0 |

Citric acid can be used to adjust the pH to a desired level.

The composition in Example 60 contains approximately 3% Cephalosporin C.

Other suitable compositions can be made in accordance with Example 60 which include cephalosporin C in the following percentages: 0.5%, 1%, 2%, 4%, 5%, and 10%.

EXAMPLE 61

A dermatological lotion containing amoxicillin is obtained by mixing the following ingredients in the amounts specified. The ingredients in Container A is blended with the ingredients in Container B.

| Ingredient | Weight Percent of ingredient in overall lotion |
| --- | --- |
| In Container A: | |
| Ethoxylated cetyl-stearyl alcohol | 7.00 |
| Cetyl alcohol | 0.75 |
| Isopropyl myristate | 5.00 |
| Butylated hydroxyanisole | 0.10 |
| Polyoxyl 40 stearate | 0.25 |
| Water, deionized or distilled | 70.80 |
| Propylene glycol | 3.00 |
| Acetone | 7.00 |
| Dioctyl sodium sulfosuccinate | 0.10 |
| In Container B: | |
| Acetone | 3.00 |
| amoxicillin | 3.00 |

Citric acid can be used to adjust the pH to a desired level.

To obtain the lotion composition in Example 61, the composition in Container A is prepared. This composition in Container A is stable for long periods of time.

Container B can contain only amoxicillin for a long period of time. Just prior to forming the complete lotion composition, 3 grams of acetone are added to Container B to dissolve the amoxicillin. Then, the contents of Container A and Container B are combined to form the complete lotion composition of the invention.

The composition in Example 61 contains approximately 3% amoxicillin.

Other suitable compositions can be made in accordance with Example 61 which include amoxicillin in the following percentages: 0.5%, 1%, 2%, 4%, 5%, and 10%.

EXAMPLE 62

A dermatological lotion containing cephalosporin C is obtained by mixing the following ingredients in the amounts specified. The ingredients in Container A is blended with the ingredients in Container B.

| Ingredient | Weight Percent of ingredient in overall lotion |
| --- | --- |
| In Container A: | |
| Ethoxylated cetyl-stearyl alcohol | 7.00 |
| Cetyl alcohol | 0.75 |
| Isopropyl myristate | 5.00 |
| Butylated hydroxyanisole | 0.10 |
| Polyoxyl 40 stearate | 0.25 |
| Water, deionized or distilled | 70.80 |
| Propylene glycol | 3.00 |
| Acetone | 7.00 |
| Dioctyl sodium sulfosuccinate | 0.10 |
| In Container B: | |
| Acetone | 3.00 |
| cephalosporin C | 3.00 |

Citric acid can be used to adjust the pH to a desired level.

To obtain the lotion composition in Example 62, the composition in Container A is prepared. This composition in Container A is stable for long periods of time.

Container B can contain only cephalosporin C for a long period of time. Just prior to forming the complete lotion composition, 3 grams of acetone are added to Container B to dissolve the cephalosporin C. Then, the contents of Container A and Container B are combined to form the complete lotion composition of the invention.

The composition in Example 62 contains approximately 3% cephalosporin C.

Other suitable compositions can be made in accordance with Example 62 which include cephalosporin C in the following percentages: 0.5%, 1%, 2%, 4%, 5%, and 10%.

EXAMPLE 63

A dermatological lotion is obtained by mixing the following ingredients in the amounts specified:

| Ingredient | Weight Percent |
| --- | --- |
| Ethoxylated cetyl-stearyl alcohol | 7 |
| Cetyl alcohol | 0.75 |
| Isostearyl neopentanoate | 5 |
| Butylated hydroxyanisole | 0.10 |
| Polyoxyl 40 stearate | 0.25 |
| Water, deionized or distilled | 71.8 |
| Propylene glycol | 3 |
| Acetone | 10 |
| Dioctyl sodium sulphosuccinate | 0.1 |
| Ampicillin | 2 |

Other suitable compositions can be made in accordance with Example 63 which include ampicillin in the following percentages: 0.5%, 1%, 3%, 4%, 5%, and 10%.

EXAMPLE 64

A dermatological lotion is obtained by mixing the following ingredients in the amounts specified:

| Ingredient | Weight Percent |
| --- | --- |
| Ethoxylated cetyl-stearyl alcohol | 7 |
| Cetyl alcohol | 0.75 |
| Decyl oleate | 5 |
| Butylated hydroxyanisole | 0.10 |
| Polyoxyl 40 stearate | 0.25 |
| Water, deionized or distilled | 71.8 |
| Propylene glycol | 3 |
| Acetone | 10 |
| Dioctyl sodium sulphosuccinate | 0.1 |
| Ampicillin | 2 |

Other suitable compositions can be made in accordance with Example 64 which include ampicillin in the following percentages: 0.5%, 1%, 3%, 4%, 5%, and 10%.

EXAMPLE 65

A lotion composition is obtained as follows. Mix the following ingredients in the amounts specified.

| Ingredient | Weight Percent |
| --- | --- |
| Ethoxylated cetyl-stearyl alcohol | 7 |
| Cetyl alcohol | 0.75 |
| Isostearyl neopentanoate | 5 |
| Butylated hydroxyanisole | 0.10 |
| Polyoxyl 40 stearate | 0.25 |
| Water, deionized or distilled | 66.8 |
| Propylene glycol | 3 |
| Benzoyl peroxide (micronized) | 5 |
| Acetone | 10 |
| Dioctyl sodium sulphosuccinate | 0.1 |
| Ampicillin | 2 |

Other suitable compositions can be made in accordance with Example 65 which include ampicillin in the following percentages: 0.5%, 1%, 3%, 4%, 5%, and 10%.

EXAMPLE 66

A lotion composition is obtained as follows. Mix the following ingredients in the amounts specified.

| Ingredient | Weight Percent |
| --- | --- |
| Ethoxylated cetyl-stearyl alcohol | 7 |
| Cetyl alcohol | 0.75 |
| Decyl oleate | 5 |
| Butylated hydroxyanisole | 0.10 |
| Polyoxyl 40 stearate | 0.25 |
| Water, deionized or distilled | 66.8 |
| Propylene glycol | 3 |
| Benzoyl peroxide (micronized) | 5 |
| Acetone | 10 |
| Dioctyl sodium sulphosuccinate | 0.1 |
| Ampicillin | 2 |

Other suitable compositions can be made in accordance with Example 66 which include ampicillin in the following percentages: 0.5%, 1%, 3%, 4%, 5%, and 10%.

EXAMPLE 67

A dermatological lotion is obtained by mixing the following ingredients in the amounts specified:

| Ingredient | Weight Per Cent |
|---|---|
| Ethoxylated cetyl-stearyl alcohol | 7 |
| Cetyl alcohol | 0.75 |
| Isostearyl neopentanoate | 5 |
| Butylated hydroxyanisole | 0.10 |
| Polyoxyl 40 stearate | 0.25 |
| Water, deionized or distilled | 71.8 |
| Propylene glycol | 3 |
| Acetone | 10 |
| Dioctyl sodium sulphosuccinate | 0.1 |
| Amoxicillin | 2 |

Other suitable compositions can be made in accordance with Example 67 which include amoxicillin in the following percentages: 0.5%, 1%, 3%, 4%, 5%, and 10%.

EXAMPLE 68

A dermatological lotion is obtained by mixing the following ingredients in the amounts specified:

| Ingredient | Weight Per Cent |
|---|---|
| Ethoxylated cetyl-stearyl alcohol | 7 |
| Cetyl alcohol | 0.75 |
| Decyl oleate | 5 |
| Butylated hydroxyanisole | 0.10 |
| Polyoxyl 40 stearate | 0.25 |
| Water, deionized or distilled | 71.8 |
| Propylene glycol | 3 |
| Acetone | 10 |
| Dioctyl sodium sulphosuccinate | 0.1 |
| Amoxicillin | 2 |

Other suitable compositions can be made in accordance with Example 68 which include amoxicillin in the following percentages: 0.5%, 1%, 3%, 4%, 5%, and 10%.

EXAMPLE 69

A cream composition is obtained as follows. Mix the following ingredients in the amounts specified.

| Ingredient | Weight Per Cent |
|---|---|
| Ethoxylated cetyl-stearyl alcohol | 15 |
| Cetyl alcohol | 1.25 |
| Isostearyl neopentanoate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| Ampicillin | 3 |

Other suitable compositions can be made in accordance with Example 69 which include ampicillin in the following percentages: 0.5%, 1%, 2%, 4%, 5%, and 10%.

EXAMPLE 70

A cream composition is obtained as follows. Mix the following ingredients in the amounts specified.

| Ingredient | Weight Per Cent |
|---|---|
| Ethoxylated cetyl-stearyl alcohol | 15 |
| Cetyl alcohol | 1.25 |
| Decyl oleate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| Ampicillin | 3 |

Other suitable compositions can be made in accordance with Example 70 which include ampicillin in the following percentages: 0.5%, 1%, 2%, 4%, 5%, and 10%.

EXAMPLE 71

A lotion composition is obtained as follows. Mix the following ingredients in the amounts specified.

| Ingredient | Weight Per Cent |
|---|---|
| Ethoxylated cetyl-stearyl alcohol | 7 |
| Cetyl alcohol | 0.75 |
| Isostearyl neopentanoate | 5 |
| Butylated hydroxyanisole | 0.10 |
| Polyoxyl 40 stearate | 0.25 |
| Water, deionized or distilled | 66.8 |
| Propylene glycol | 3 |
| Benzoyl peroxide (micronized) | 5 |
| Acetone | 10 |
| Dioctyl sodium sulphosuccinate | 0.1 |
| Amoxicillin | 2 |

Other suitable compositions can be made in accordance with Example 71 which include amoxicillin in the following percentages: 0.5%, 1%, 3%, 4%, 5%, and 10%.

EXAMPLE 72

A lotion composition is obtained as follows. Mix the following ingredients in the amounts specified.

| Ingredient | Weight Per Cent |
|---|---|
| Ethoxylated cetyl-stearyl alcohol | 7 |
| Cetyl alcohol | 0.75 |
| Decyl oleate | 5 |
| Butylated hydroxyanisole | 0.10 |
| Polyoxyl 40 stearate | 0.25 |
| Water, deionized or distilled | 66.8 |
| Propylene glycol | 3 |
| Benzoyl peroxide (micronized) | 5 |
| Acetone | 10 |
| Dioctyl sodium sulphosuccinate | 0.1 |
| Amoxicillin | 2 |

Other suitable compositions can be made in accordance with Example 72 which include amoxicillin in the following percentages: 0.5%, 1%, 3%, 4%, 5%, and 10%.

EXAMPLE 73

A cream composition is obtained as follows. Mix the following ingredients in the amounts specified.

| Ingredient | Weight Per Cent |
|---|---|
| Ethoxylated cetyl-stearyl alcohol | .15 |
| Cetyl alcohol | 1.25 |
| Isostearyl neopentanoate | 5 |
| Butylated hydroxyanisole | 0.10 |

-continued

| Ingredient | Weight Per Cent |
|---|---|
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| Amoxicillin | 3 |

Other suitable compositions can be made in accordance with Example 73 which include amoxicillin in the following percentages: 0.5%, 1%, 2%, 4%, 5%, and 10%.

EXAMPLE 74

A cream composition is obtained as follows. Mix the following ingredients in the amounts specified.

| Ingredient | Weight Per Cent |
|---|---|
| Ethoxylated cetyl-stearyl alcohol | 15 |
| Cetyl alcohol | 1.25 |
| Decyl oleate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| Amoxicillin | 3 |

Other suitable compositions can be made in accordance with Example 74 which include amoxicillin in the following percentages: 0.5%, 1%, 2%, 4%, 5%, and 10%.

EXAMPLE 75

A lotion composition is obtained as follows. Mix the following ingredients in the amounts specified.

| Ingredient | Weight Per Cent |
|---|---|
| Ethoxylated cetyl-stearyl alcohol | 7 |
| Cetyl alcohol | 0.75 |
| Isostearyl neopentanoate | 5 |
| Butylated hydroxyanisole | 0.10 |
| Polyoxyl 40 stearate | 0.25 |
| Water, deionized or distilled | 66.8 |
| Propylene glycol | 3 |
| Benzoyl peroxide (micronized) | 5 |
| Acetone | 10 |
| Dioctyl sodium sulphosuccinate | 0.1 |
| Cephalosporin C | 2 |

Other suitable compositions can be made in accordance with Example 75 which include cephalosporin C in the following percentages: 0.5%, 1%, 3%, 4%, 5%, and 10%.

EXAMPLE 76

A lotion composition is obtained as follows. Mix the following ingredients in the amounts specified.

| Ingredient | Weight Per Cent |
|---|---|
| Ethoxylated cetyl-stearyl alcohol | 7 |
| Cetyl alcohol | 0.75 |
| Decyl oleate | 5 |
| Butylated hydroxyanisole | 0.10 |
| Polyoxyl 40 stearate | 0.25 |
| Water, deionized or distilled | 66.8 |
| Propylene glycol | 3 |
| Benzoyl peroxide (micronized) | 5 |
| Acetone | 10 |
| Dioctyl sodium sulphosuccinate | 0.1 |
| Cephalosporin C | 2 |

Other suitable compositions can be made in accordance with Example 76 which include cephalosporin C in the following percentages: 0.5%, 1%, 3%, 4%, 5%, and 10%.

EXAMPLE 77

A cream composition is obtained as follows. Mix the following ingredients in the amounts specified.

| Ingredient | Weight Per Cent |
|---|---|
| Ethoxylated cetyl-stearyl alcohol | 15 |
| Cetyl alcohol | 1.25 |
| Isostearyl neopentanoate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| Cephalosporin C | 3 |

Other suitable compositions can be made in accordance with Example 77 which include cephalosporin C in the following percentages: 0.5%, 1%, 2%, 4%, 5%, and 10%.

EXAMPLE 78

A cream composition is obtained as follows. Mix the following ingredients in the amounts specified.

| Ingredient | Weight Per Cent |
|---|---|
| Ethoxylated cetyl-stearyl alcohol | 15 |
| Cetyl alcohol | 1.25 |
| Decyl oleate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| Cephalosporin C | 3 |

Other suitable compositions can be made in accordance with Example 78 which include cephalosporin C in the following percentages: 0.5%, 1%, 2%, 4%, 5%, and 10%.

EXAMPLE 79

An oil-in-water emulsion containing amoxicillin in ointment form is obtained as follows.

Part A is comprised of a 3.33% aqueous solution of amoxicillin.

Part B is an ointment base comprised of:

| Ingredient | Weight Per Cent |
|---|---|
| viscid paraffin | 35 |
| white vaseline | 35 |

| Ingredient | Weight Per Cent |
|---|---|
| cetylstearyl alcohol | 30 |

A mixture is obtained as follows. Mix 60 ml. of Part A is mixed with 40 ml. of Part B to provide an oil-in-water emulsion in ointment form containing approximately 2% amoxicillin.

Other suitable compositions can be made in accordance with Example 79 which include amoxicillin in the following percentages: 0.5%, 1%, 3%, 4%, 5%, and 10%.

EXAMPLE 80

A mineral-oil-based amoxicillin ointment is obtained as follows.

Part A is comprised of a 6.66% aqueous solution of amoxicillin.

Part B is an ointment base comprised of:

| Ingredient | Parts |
|---|---|
| glycerin | 5 |
| isopropyl alcohol, 96% | 5 |
| mineral oil | 60 |

A mixture is obtained as follows. Mix 30 ml. of Part A with 70 ml. of Part B to provide a mineral-oil-based ointment containing approximately 2% amoxicillin.

Other suitable compositions can be made in accordance with Example 80 which include amoxicillin in the following percentages: 0.5%, 1%, 3%, 4%, 5%, and 10%.

EXAMPLE 81

An oil-in-water emulsion containing cephalosporin C in ointment form is obtained as follows.

Part A is comprised of a 3.33% aqueous solution of cephalosporin C.

Part B is an ointment base comprised of:

| Ingredient | Weight Per Cent |
|---|---|
| viscid paraffin | 35 |
| white vaseline | 35 |
| cetylstearyl alcohol | 30 |

A mixture is obtained as follows. Mix 60 ml. of Part A is mixed with 40 ml. of Part B to provide an oil-in-water emulsion in ointment form containing approximately 2% cephalosporin C.

Other suitable compositions can be made in accordance with Example 81 which include cephalosporin C in the following percentages: 0.5%, 1%, 3%, 4%, 5%, and 10%.

EXAMPLE 82

A mineral-oil-based cephalosporin C ointment is obtained as follows.

Part A is comprised of a 6.66% aqueous solution of cephalosporin C.

Part B is an ointment base comprised of:

| Ingredient | Parts |
|---|---|
| glycerin | 5 |
| isopropyl alcohol, 96% | 5 |
| mineral oil | 60 |

A mixture is obtained as follows. Mix 30 ml. of Part A with 70 ml. of Part B to provide a mineral-oil-based ointment containing approximately 2% cephalosporin C.

Other suitable compositions can be made in accordance with Example 82 which include cephalosporin C in the following percentages: 0.5%, 1%, 3%, 4%, 5%, and 10%.

A number of patients having acne vulgaris have been successfully treated with 2% topical ampicillin, and the case histories are described as follows.

Patient number one is a male and began treatment at the age of sixteen for acne vulgaris. Over the course of one year, he had been treated with the following agents in the order specified: first, tretinoin and 3% erythromycin/5% benzoyl peroxide gel topically; second, oral ampicillin in conjunction with topical erythromycin solution and topical tretinoin (it is noted that therapeutic doses of oral ampicillin gave the patient diarrhea); third, low dose oral ampicillin (250 mgm per day) in conjunction with topical tretinoin and topical clindamycin solution; fourth, tretinoin and clindamycin solution alone without any oral medication. Then the severity of the patient's acne worsened.

Then, photos were taken of the patient's right and left facial cheeks. The physical exam revealed on the face 2+ papules on a scale of 0-3+ and 2+ pustules on a scale of 0-3+. It is noted that the scale used for describing the symptoms of acne herein is an adaptation of the scale described on page 611 of Bleicher, P., Charles, J., and Sober, A., "Topical Metronidazole Therapy for Rosacea", *Arch Dermatol.* 1987, vol. 123, pages 609-614.

At this point topical clindamycin was discontinued, and 2% ampicillin in a vehicle known as "Neutrogena Vehicle N (mild)" made by Neutrogena Dermatologics Division of Neutrogena Corporation, Los Angeles, Calif., (the mixture of ampicillin and the vehicle containing approximately: ethyl alcohol (41.5% by weight), Laureth (0.5% by weight), isopropyl alcohol (6.0% by weight), ampicillin (2.0% by weight), and purified water (50.0% by weight)) was prescribed topically, in accordance with the invention, along with tretinoin topically. Approximately seven weeks later, the patient subjectively indicated that his condition was improving. Also, at this time, a physical examination was conducted which revealed on the face 1+ papules and only one pustule on the left cheek (0.5+ pustules). This constituted a 50% improvement over a period of seven weeks with the invention in contrast to negligible improvement with prior art treatments over the course of more than one year. Photos were again taken.

The second patient is a female, and at the time of first treatment was 12 years old. She had acne vulgaris which was treated with the following combinations of treatments over a two year period in the order specified: first, a combination of topical tretinoin and 3% erythromycin/5% benzoyl peroxide gel; second, oral ampicillin in conjunction with tretinoin, topical clindamycin solution, and topical benzoyl peroxide; third, topical clindamycin and topical tretinoin and a 2% salicylic acid wash. At this point her acne vulgaris flared and on physical examination of her face, she had 2+ comedones on a scale of 0–3+, 2+ pustules on a scale of 0–3+, and 2+ papules on a scale of 0–3+.

At this point, photos were taken of her right and left facial cheeks. Then, in accordance with the invention, she was placed on 2% topical ampicillin (in admixture as described above in the treatment of the first patient) twice daily to her face, and she continued with topical tretinoin and salicylic acid wash.

Seven weeks later she was examined. The patient indicated that her acne cleared within a two and one-half to three week period after commencing the treatment with topical ampicillin. On physical examination, her face revealed 1+ comedones, 0.5+ papules, and 0 pustules. The visual impression was a dramatic clearing (approximately 75% reduction) of her acne vulgaris. Again, photos were taken. With the composition and method of the invention, there was a 75% improvement over a period of a mere seven weeks in contrast to prior art treatments over a period of two years which resulted in only a negligible improvement. Photos were again taken.

The third patient is a female first examined at age 28 for the treatment of acne vulgaris. Prior to this examination, and over a period of 12 years, she was treated for acne vulgaris. Several months prior to this examination, for her facial acne, she was treated with topical tretinoin, 3% erythromycin/5% benzoyl peroxide gel, and an oral sulfa drug whose generic name is trimethoprim-sulfamethoxazole.

Upon this examination of the third patient, she had 1+ comedones, 1+ pustules, and 1+ papules. She was prescribed oral ampicillin and continued the other topical medications. Upon physical examination two months later, she had 1+ papules and 0+ comedones. She was improved.

This patient was to start taking a birth control pill (Orthonovum, 1/35) for oral contraception. Due to the possible side effects of oral antibiotic decreasing the effectiveness of the birth control pill, the patient elected to stop the oral ampicillin. The patient was placed on topical benzoyl peroxide, topical clindamycin gel, and continued on topical tretinoin. 3% erythromycin/5% benzoyl peroxide was discontinued.

This patient was seen two months later, and upon physical examination, the patient exhibited 1+ comedones and 0.5+ papules. The patient was continued on the above-mentioned topical medications; however, the tretinoin strength was increased. The patient called approximately six weeks later to report that her acne vulgaris was flaring, and the patient was placed on oral ampicillin; and the topical medications were also continued.

This patient was seen by the inventor one month later and was noted, on physical examination, to have 2+ comedones and 2+ papules. At this point, the tretinoin was increased to 0.1% cream. All other topical medications were also continued. The oral ampicillin was reduced to just one week out of the month.

Six weeks later, upon physical examination, this patient exhibited 2+ pustules, 0.5+ papules, and 1+ comedones. The patient's acne was flaring. Again, due to the potential risk of decreasing the effectiveness of her oral contraceptive, the oral ampicillin was discontinued and the patient was started on a composition of the invention, namely 2% topical ampicillin (in admixture as described above in the treatment of the first patient).

A photo was taken prior to treatment with the topical ampicillin.

Upon treatment with the 2% ampicillin of the invention, the topical clindamycin was discontinued. The topical tretinoin and benzoyl peroxide were continued at their same doses. Approximately seven weeks later, the patient remarked that her condition had improved with the topical ampicillin. On physical examination, the patient had on her face, 0.5+ pustules on the right cheek and 0 pustules on the left cheek, 0.5+ papules, and 0.5+ comedones. The patient was approximately 50% improved clinically over the last seven weeks. Due to the success of the topical ampicillin, the patient elected to continue topical ampicillin. The other topical medications (tretinoin and benzoyl peroxide) were continued as well. Photos were again taken.

The fourth patient is a male and began treatment at age 12 for acne vulgaris. He was first treated with topical clindamycin gel and benzoyl peroxide. His acne vulgaris worsened by age 14 and required oral ampicillin 1 gram a day, topical tretinoin, and 3% erythromycin/5% benzoyl peroxide gel. The severity of the acne worsened so much by age 15 that oral isotretinoin was discussed. The parents did not want to continue systemic treatments due to potential side effects.

Then, photos were taken of the patient's right and left facial cheeks. The physical exam revealed 2+ comedones, 1+ papules and 1+ pustules. In accordance with the invention, the patient was started on topical 2% ampicillin (in admixture as described above in the treatment of the first patient) twice daily to his face, and continued on tretinoin cream.

Approximately, 3 months later the patient returned. The patient indicated that his acne improved within one month and cleared by two months time. On physical exam his face revealed 1+ comedones, 1 papule on his right cheek, 0+ papules on his left cheek (which is a score of 0.5+ papules), and 0+ pustules. This constituted a 75% improvement over a period of twelve weeks with the invention in contrast to resistance to prior art treatments over the course of three and one half years. Photos were again taken.

The fifth patient is male and began treatment at age 12 for acne vulgaris. He had been treated with oral antibiotics including oral erythromycin, oral minocycline, topical tretinoin, and benzoyl peroxide lotion. He failed this treatment regimen due to severe acne vulgaris which necessitated treatment with oral isotretinoin for 20 weeks. Upon discontinuance of oral isotretinoin, he required oral ampicillin, and topical tretinoin.

At age 14, 7 months off oral isotretinoin the patient's acne was worsening despite oral ampicillin 500 mg twice daily and topical tretinoin cream. Then photos were taken of his facial cheeks and forehead. On physical exam on his forehead and facial cheeks were 2+ papules, 1+ pustules, and 2+ comedones. He was taken off of his oral ampicillin and in accordance with the invention he was placed on 2% topical ampicillin (in admixture as described above in the treatment of the first patient) twice daily to his face, and he was continued on topical tretinoin.

Approximately 12 weeks later the patient returned for examination. The patient indicated that he improved within the first few weeks of therapy but forgot to get a new 2% topical ampicillin each month and used the same original topical ampicillin for the entire 3 months. On physical exam of his forehead and facial cheeks he had 2+ comedones, 1+ pustules on his right cheek, 0.5+ pustules on his left cheek, and 1+ papules. His acne was approximately 20% improved. The patient was educated to refill his prescription on a monthly basis to achieve better efficacy. He was continued on his topical ampicillin and his topical tretinoin was increased. Photos were taken for documentation of his forehead and facial cheeks.

The sixth patient is a female, and at the time of first treatment was 13 years old. She had acne vulgaris which was treated with topical tretinoin, topical clindamycin, and oral minocycline. Her acne worsened and necessitated a change from minocycline to oral ampicillin 1 gram a day, topical clindamycin, and topical tretinoin. Her acne improved only minimally on oral ampicillin, and her mother was concerned about her continuing on high doses of oral ampicillin.

Photos were taken of the patient's face. At this point on physical exam her face revealed 2+ comedones, 1+ pustules, 1+ inflammatory papules. Then, in accordance with the invention, she was placed on 2% topical ampicillin (in admixture as described above in the treatment of the first patient) twice daily to her face and she continued her oral ampicillin and discontinued her topical clindamycin.

Approximately 7 weeks later she was examined. The patient indicated that her acne started to clear within 2 weeks of commencing treatment with topical 2% ampicillin. On physical examination, her face revealed 1+ comedones, 0+ pustules, right cheek 0+ papules, left cheek 0.5+ papules. She was approximately 75% cleared from her previous examination seven weeks prior. Photos were again taken.

The patients in these studies were all told to refill their topical ampicillin solution every one month and to keep their medication refrigerated.

The table below (Table I) illustrates in summary form the six patients treated with the invention 2% topical ampicillin:

Example 12; 71.2% in Example 3; and 98.5% in Example 12.

Similarly, from the description of the treatment of the patients and the composition examples set forth hereinabove, the weight percent of isopropyl alcohol spans 4% to 80%. More specifically, the weight percents of isopropyl alcohol are as follows: 4.0% in Example 54; 4.3% in Example 25; 6.0% for the treated Patients; 6.0% in Example 13; and 80.0% in Example 39.

Similarly, from the description of the treatment of the patients and the composition examples set forth hereinabove, the weight percent of propylene glycol spans 3% to 26.8%. More specifically, the weight percents of propylene glycol are as follows: 3.0% in Example 6; 3.0% in Example 9; 3.0% in Example 30; 10.0% in Example 54; 10.0% in Example 39; and 26.8% in Example 3.

Similarly, from the description of the composition examples set forth hereinabove, the weight percent of glycerin is 6.9% in Example 25.

It is well known that ethyl alcohol, isopropyl alcohol, propylene glycol, and glycerin are water-miscible alcohols that can be applies topically to the skin.

It is seen in Example 12 that the carrier ingredients for the antibiotic can be one water-miscible solvent (ethyl alcohol) without the presence of water.

It is seen in Example 3 that the carrier ingredients for the antibiotic can be two water-miscible solvents (ethyl alcohol and propylene glycol) without the presence of water.

It is seen in Examples 1, 2, 4, 13, 26, 37, 38, and 42–57 that the carrier ingredients for the antibiotic can be two or more water-miscible solvents in the presence of water. The highest weight percent for two or more water-miscible solvents in the presence of water as carriers for the antibiotic can be 99.5% as disclosed in Examples 1, 2, 4, 13, 26, 37, 38, and 42–57 where 0.5% weight of the respective antibiotic can be present in the composition having 99.5% weight of the carrier.

TABLE I

| Patient #'s | Sex | Age onset of Acne | Patients treated with topical ampicillin | | Time in wks between baseline exam and Follow Up exam |
|---|---|---|---|---|---|
| | | | Baseline exam face-start 2% top. ampicillin | Follow-up exam-face 2% top. ampicillin | |
| 1 | M | 16 | 2+ papules<br>2+ pustules | 1+ papules<br>0.5+ pustules | 7 weeks |
| 2 | F | 12 | 2+ papules<br>2+ pustules<br>2+ comedones | 0.5+ papules<br>0+ pustules<br>1+ comedones | 7 weeks |
| 3 | F | 16 | 0.5+ papules<br>2+ pustules<br>1+ comedones | 0.5+ papules<br>0.5+ pustules<br>0.5+ comedones | 7 weeks |
| 4 | M | 12 | 1+ papules<br>1+ pustules<br>2+ comedones | 0.5+ papules<br>0+ pustules<br>1+ comedones | 12 weeks |
| 5 | M | 12 | 2+ papules<br>1+ pustules<br>2+ comedones | 2+ papules<br>1+ pustules Right cheek<br>0.5+ pustules Left cheek<br>2+ comedones | 12 weeks |
| 6 | F | 13 | 1+ papules<br>1+ pustules<br>2+ comedones | 0+ papules Right cheek<br>0.5+ papules Left cheek<br>0+ pustules<br>1+ comedones | 7 weeks |

From the description of the treatment of the patients and the composition examples set forth hereinabove, the weight percent of ethyl alcohol spans 35% to 98.5%. More specifically, the weight percents of ethyl alcohol are as follows: 35.0% in Example 17; 35.0% in Example 16; 41.5% for the treated Patients; 42.0% in Example 1; 44.0% in Example 13; 48.0% in Example 54; 65.0% in From the description of the treatment of the patients and the composition examples set forth hereinabove, the sums of the weight percents of water and water-miscible alcohols selected from the group consisting of ethyl alcohol, isopropyl alcohol, propylene glycol, and glycerin span 42.2% to 99.5%. More specifically, the sums of the weight percents of water and the water-miscible alcohols selected from the group consisting of ethyl alcohol, isopropyl alcohol, propylene glycol, and glycerin are as follows: 42.5% in Example 25; 73.8% in Example 30; 74.8% in Example 9; 86.6% in Example 16; 90.0% in Example 17; 97.5% for the treated Patients; 98.0% in Example 6; 98.5% in Example 54; 99.0% in Example 39; and 99.5% in Example 13.

Thus, the widest range for a water-miscible alcohol either alone, or in combination with another water-miscible alcohol or water, in weight percent, is 42.2% to 99.5%.

Similarly, from the description of the treatment of the patients and the composition examples set forth hereinabove, the sums of the weight percents of the water-miscible alcohols (ethyl alcohol, isopropyl alcohol, propylene glycol, and glycerin) span 11.2% to 90%. More specifically, the sums of the weight percents of the water-miscible alcohols are as follows: 11.2% in Example 25; 47.5% for the treated Patients; 50.0% in Example 13; 62.0% in Example 54; and 90.0% in Example 39.

Similarly, from the description of the treatment of the patients and the composition examples set forth hereinabove, the weight percent of water spans 9% to 95%. More specifically, the weight percents of water are as follows: 9.0% in Example 39; 31.0% in Example 25; 36.5% in Example 54, 49.5% in Example 13; 50.0% of the treated Patients; 51.6% in Example 16; 55.0% in Example 17; 57.3% in Example 15; 66.8% in Example 14; 70.8% in Example 30; 71.8% in Example 9; and 95.0% in Example 6.

It is noted that, compositions containing carrier ingredients, wherein at least one carrier ingredient is selected from the group consisting of water and a water-miscible alcohol, and wherein the combined weight percents of the carrier ingredients is in a range spanning 42.2% to 99.5%, covers lotions, creams gels, and oil-in-water emulsions. More specifically, this range of carrier ingredients covers:

the lotions in Examples 9, 10, 14, 20, 30, 33, 39, 40, 41, 61, 62, 63, 64, 65, 66, 67, 68, 71, 72, 75, and 76;

the creams in Examples 15, 21, 34, 69, 70, 73, 74, 77, and 78;

the gels in Examples 5, 6, 7, 8, 16, 22, 28, 29, 35, 58, 59, and 60; and the oil-in-water emulsion ointments in Examples 24 (62.3% water), 25 (42.2% water), 79 (62.3% water), 80 (42.2% water), and 82 (42.2% water). The foregoing description of the invention has been presented for purposes of illustration and description. It is not intended t be exhaustive or to limit the invention to the precise forms disclosed. Obvious modifications or variations of the methods and compositions of the invention are possible in light of the above teachings. The embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

We claim:

1. A method of treating a human being for acne vulgaris which comprises administering to the human being an amount of a composition consisting essentially of an aminopenicillin antibiotic active ingredient selected from the group consisting of ampicillin and amoxicillin and a pharmaceutical carrier, applied directly to affected dermal tissues, effective to treat the acne, wherein the carrier includes water and a water-miscible alcohol, wherein a combined weight percent of said water and water-miscible alcohol is in a range spanning 42.2% to 99.5% of the composition.

2. The method described in claim 1 wherein the aminopenicillin antibiotic is selected from the group consisting of ampicillin; ampicillin, monohydrate; ampicillin, potassium salt; ampicillin, sesquihydrate; ampicillin, trihydrate; ampicillin, anhydrous form; ampicillin, sodium salt and ampicillin, D(−)form, L(+)form, or DL-form.

3. The method described in claim 1 wherein the aminopenicillin antibiotic is selected from the group consisting of amoxicillin; amoxicillin trihydrate; amoxicillin hydrochloride trihydrate and amoxicillin beta-naphthalenesulfonate trihydrate.

4. The method described in claim 1 wherein the carrier is present in a weight percent range spanning 73.8% to 99.5%.

5. The method described in claim 1 wherein the carrier is present in a weight percent range spanning 42.2% to 99.5% and includes water, ethyl alcohol, and isopropyl alcohol.

6. The method described in claim 1 wherein the carrier includes ethyl alcohol in a weight percent range spanning 35% to 98.5%.

7. The method described in claim 1 wherein the carrier includes isopropyl alcohol in a weight percent range spanning 4% to 80%.

8. The method described in claim 1 wherein the carrier includes propylene glycol in a weight percent range spanning 3% to 26.8%.

9. The method described in claim 1 wherein the carrier includes water in a weight percent range spanning 9% to 95%.

10. The method described in claim 1 wherein the carrier includes at least one water-miscible alcohol in a weight percent range spanning 11.2% to 90%.

11. The method described in claim 1 wherein the carrier includes water, at least one water-miscible alcohol, and mineral oil.

12. The method described in claim 1 wherein the carrier is present in a weight percent range spanning 42.2% to 99.5% and includes water in a weight percent range spanning 9% to 95%, ethyl alcohol in a weight percent range spanning 35% to 98.5%, and isopropyl alcohol in a weight percent range spanning 4% to 80%.

13. A method of treating a human being for acne vulgaris which comprises the steps of:

topically administering to affected dermal areas of the human being an amount of at least one conventionally topically applied anti-acne medication selected from the group consisting of benzoyl peroxide, sulfur, recorcinol, salicyclic acid, and tretinoin in conventional doses, and topically administering to the affected dermal areas a composition consisting essentially of an amount of an ampicillin antibiotic, effective to treat the acne, wherein the antibiotic is present in a range of 0.5% to 10% by weight of the composition including a carrier which includes water and a water-miscible alcohol, wherein a combined weight percent of said water and water-miscible alcohol is in a range spanning 42.2% to 99.5% of the composition.

14. A method of treating a human being for acne vulgaris which comprises the steps of:

topically administering to affected dermal areas of the human being an amount of at least one conventionally topically administered conventional anti-acne medication selected from the group consisting of benzoyl peroxide and tretinoin in conventional doses, and topically administering to the affected dermal areas an amount of a composition consisting essentially of an aminopenicillin antibiotic active ingredient selected from the group consisting of ampicillin and amoxicillin and a pharmaceutical carrier, effective to treat the acne, wherein the antibiotic is present in a range of 0.5% to 10% by weight of the composition, wherein the carrier includes water and a water-miscible alcohol, wherein a combined weight percent of said water and water-miscible alcohol is in a range spanning 42.2% to 99.5% of the composition.

15. The method of treating a human being as described in claim 5 wherein the aminopenicillin is ampicillin.

16. A method of treating a human being for acne vulgaris which comprises administering to the human being an amount of a composition consisting essentially of an ampicillin antibiotic active ingredient and a pharmaceutical carrier, the composition applied topically directly to affected dermal tissues, the composition being effective to treat the acne.
wherein the carrier includes water and a water-miscible alcohol, wherein a combined weight percent of said water and water-miscible alcohol is in a range spanning 42.2% to 99.5% of the composition.

17. The method described in claim 16 wherein the ampicillin antibiotic is present in a range of from 0.5% to 10% by weight of the composition.

18. A method of treating a human being for acne vulgaris which comprises administering to the human being an amount of a composition consisting essentially of an aminopenicillin antibiotic active ingredient selected from the group consisting of ampicillin and amoxicillin and a pharmacuetical carrier, applied directly to affected dermal tissues, said aminopenicillin antibiotic being present in a range of from 0.5% to 10% by weight of the composition, effective to treat the acne, wherein the carrier includes water and a water-miscible alcohol, wherein a combined weight percent of said water and water-miscible alcohol is in a range spanning 42.2% to 99.5% of the composition.

19. A method of treating a human being for acne vulgaris which comprises administering to the human being an amount of a composition consisting essentially of an antibiotic selected from the group consisting of ampicillin, monohydrate; ampicillin, potassium salt; ampicillin, sesquihydrate; ampicillin, trihydrate; ampicillin, anhydrous form; ampicillin, sodium salt; ampicillin, D(−)form, L(+)form, or DL-form, in range of from 0.5% to 10% by weight of a composition, and a carrier, applied directly to affected dermal tissues, effective to treat the acne and acneiform dermal disorders, wherein the carrier includes water and a water-miscible alcohol, wherein a combined weight percent of said water and water-miscible alcohol is in a range spanning 42.2% to 99.5% of the composition.

20. A method of treating a human being for acne vulgaris which comprises administering to the human being an amount of an anti-acne ingredient consisting essentially of an ampicillin antibiotic active ingredient, applied directly to affected dermal tissues, effective to treat the acne, wherein the antibiotic is present in a range of 0.5% to 10% by weight of a composition including a pharmaceutical carrier which includes water and a water-miscible alcohol, wherein a combined weight percent of said water and water-miscible alcohol is in a range spanning 42.2% to 99.5% of the composition.

21. The method described in claim 20 wherein the ampicillin antibiotic is applied in a water-miscible carrier including at least one water-miscible alcohol, wherein the weight percent of the at least one water-miscible alcohol is in a range spanning 11.2% to 90%.

22. The method described in claim 20 wherein the ampicillin antibiotic is applied in a water-miscible carrier including at least two water-miscibler alcohol, wherein the sum of the weight percents of the at least two water-miscible alcohols is in a range spanning 11.2% to 90%.

23. A method of treating a human being for acne vulgaris which comprises the step of:
topically administering to affected dermal areas of the human being an amount of a composition consisting essentially of benzoyl peroxide and an ampicillin antibiotic active ingredients, effective to treat the acne, wherein the composition is applied in a pharmaceutical carrier which includes water and a water-miscible alcohol, wherein a combined weight percent of said water and water-miscible alcohol is in a range spanning 42.2% to 99.5%.

24. The method described in claim 23 wherein:
the ampicillin antibiotic is present in a range spanning 0.5% to 10% by weight; and
the benzoyl peroxide is present in a range spanning 1% to 30% by weight.

25. A method of treating a human being for acne vulgaris which comprises the step of:
topically administering to affected dermal areas of the human being an amount of a composition consisting essentially of benzoyl peroxide and an aminopenicillin antibiotic active ingredients, wherein the aminopenicillin antibiotic is selected from the group consisting of ampicilin and amoxicillin, effective to treat the acne, wherein the composition is applied in a pharmaceutical carrier which includes water and a water-miscible alcohol, wherein a combined weight percent of said water and water-miscible alcohol is in a range spanning 42.2% to 99.5%.

26. The method described in claim 25 wherein the aminopenicillin antibiotic is an ampicillin.

27. The method described in claim 25 wherein:
the antibiotic is present in a range spanning 0.5% to 10% by weight; and
the benzoyl peroxide is present in a range spanning 1% to 30% by weight.

28. A method of treating a human being for acne vulgaris which comprises administering to the human being an amount of an ampicillin antibiotic, applied directly to affected dermal tissues, effective to treat the acne, wherein the antibiotic is present in an amount of 2% by weight and is applied in a carrier comprised of:
ethyl alcohol, 42.5% by weight,
Laureth-4, 0.5% by weight,
isopropyl alcohol, 6% by weight, and
water, 50% by weight.

29. A method of treating a human being for acne vulgaris which comprises administering to the human being an amount of a composition consisting essentially of an ampicillin antibiotic active ingredient benzoyl peroxide active ingredient, and a pharmaceutical carrier, applied directly to affected dermal tissues, effective to treat the acne, wherein:

the ampicillin antibiotic is present in an amount of 3% by weight, the benzoyl peroxide is present in an amount of 5% by weight, and the carrier is a gel vehicle present in an amount of 92% by weight.

30. The method described in claim 29 wherein the gel vehicle is comprises as follows:

| Ingredient in gel carrier | Weight Per Cent in the Final Mixture containing antibiotic, benzoyl peroxide, and gel carrier |
| --- | --- |
| Butylated hydroxyanisole | 0.10 |
| Colloidal Bentonite | 2.50 |
| Carboxy vinyl polymer (acid form) | 1.00 |
| Water, deionized or distilled | 54.65 |
| Diisopropanolamine | 0.75 |
| Ethyl alcohol | 32.00 |
| Dioctyl sodium sulfosuccinate | 1.00. |

31. A method of treating a human being for acne vulgaris which comprises administering to the human being an amount of an aminopenicillin antibiotic selected from the group consisting of ampicillin and amoxicillin, applied directly to affected dermal tissues, effective to treat the acne, wherein the antibiotic is present in an amount of 2% by weight and is applied in a carrier comprised of:

ethyl alcohol, 42.5% by weight,

Laureth-4, 0.5% by weight, isopropyl alcohol, 6% by weight, and water, 50% by weight.

32. A method of treating a human being for acne vulgaris which comprises administering to the human being an amount of a composition consisting essentially of an aminopenicillin antibiotic and benzoyl peroxide active ingredients, wherein the aminopenicillin antibiotic is selected from the group consisting of ampicillin and amoxicillin, and wherein the composition is administered in admixture with a pharmaceutical carrier, wherein the composition and the carrier mixture is applied directly to affected dermal tissues, in an amount effective to treat the acne, wherein:

the antibiotic is present in an amount of 3% by weight, the benzoyl peroxide is present in an amount of 5% by weight, and the carrier is a gel vehicle present in an amount of 92% by weight.

33. The method described in claim 32 wherein the gel vehicle is comprises as follows:

| Ingredient in gel carrier | Weight Per Cent in the Final Mixture containing antibiotic, benzoyl peroxide, and gel carrier |
| --- | --- |
| Butylated hydroxyanisole | 0.10 |
| Colloidal Bentonite | 2.50 |
| Carboxy vinyl polymer (acid form) | 1.00 |
| Water, deionized or distilled | 54.65 |
| Diisopropanolamine | 0.75 |
| Ethyl alcohol | 32.00 |
| Dioctyl sodium sulfosuccinate | 1.00. |

34. The method of treating a human being for acne vulgaris which comprises administering to the human being an amount of a composition consisting essentially of an aminopenicillin antibiotic active ingredient selected from the group consisting of ampicillin and amoxicillin, and a pharmaceutical carrier, applied directly to affected dermal tissues, effective to treat the acne wherein the carrier includes water and a water-miscible alcohol.

35. A method of treating a human being for acne vulgaris which comprises administering to the human being an amount of a composition consisting essentially of an ampicillin antibiotic active ingredient and a pharmaceutical carrier, applied directly to affected dermal tissues, effective to treat the acne wherein the carrier includes water and a water-miscible alcohol.

36. A method of treating a human being for acne vulgaris which comprises administering to the human being an amount of a composition consisting essentially of an amicillin antibiotic active ingredient selected from the group consisting of ampicillin, monohydrate; ampicillin, potassium salt; ampicillin, sesquihydrate; ampicillin, trihydrate; ampicillin, amhydrous form; ampicillin, sodium salt; ampicillin, D(−)form, L(+)form, or DL-form; and a pharmaceutical carrier, applied directly to affected dermal tissues, effective to treat the acne wherein the carrier includes water and a water-miscible alcohol.

* * * * *